(12) United States Patent
Zhao et al.

(10) Patent No.: US 11,385,240 B2
(45) Date of Patent: Jul. 12, 2022

(54) REAGENTS AND METHODS FOR DETECTING PROTEIN LYSINE 3-HYDROXYBUTYRYLATION

(71) Applicant: PTM BIO LLC, Chicago, IL (US)

(72) Inventors: Yingming Zhao, Chicago, IL (US); Zhongyu Xie, Chicago, IL (US)

(73) Assignee: PTM BIO LLC, Chicago, IL (US)

( * ) Notice: Subject to any disclaimer, the term of this patent is extended or adjusted under 35 U.S.C. 154(b) by 144 days.

(21) Appl. No.: 16/454,686

(22) Filed: Jun. 27, 2019

(65) Prior Publication Data

US 2019/0331695 A1    Oct. 31, 2019

Related U.S. Application Data

(62) Division of application No. 14/121,311, filed on Aug. 18, 2014, now abandoned.

(60) Provisional application No. 61/866,725, filed on Aug. 16, 2013.

(51) Int. Cl.
| | |
|---|---|
| *G01N 33/68* | (2006.01) |
| *C07K 14/47* | (2006.01) |
| *C07K 14/395* | (2006.01) |
| *C07K 14/44* | (2006.01) |
| *C07K 14/435* | (2006.01) |
| *C07K 16/18* | (2006.01) |
| *C07K 1/107* | (2006.01) |

(52) U.S. Cl.
CPC ....... *G01N 33/6875* (2013.01); *C07K 1/1077* (2013.01); *C07K 14/395* (2013.01); *C07K 14/43545* (2013.01); *C07K 14/43581* (2013.01); *C07K 14/44* (2013.01); *C07K 14/47* (2013.01); *C07K 16/18* (2013.01); *G01N 2440/10* (2013.01); *G01N 2440/24* (2013.01)

(58) Field of Classification Search
CPC ........... G01N 33/6875; G01N 2440/10; G01N 2440/24; C07K 1/1077; C07K 14/395; C07K 14/43545; C07K 14/43581; C07K 14/44; C07K 14/47; C07K 16/18
See application file for complete search history.

(56) References Cited

U.S. PATENT DOCUMENTS

| 9,625,467 B2 | 4/2017 | Zhao |
|---|---|---|
| 2008/0241862 A1 | 10/2008 | Zhao et al. |
| 2009/0075284 A1 | 3/2009 | Chinnaiyan et al. |

FOREIGN PATENT DOCUMENTS

| CN | 102375065 A | 3/2012 | |
|---|---|---|---|
| WO | 2012024612 A1 | 2/2012 | |
| WO | WO-2012024612 A1 * | 2/2012 | ....... G01N 33/57415 |

OTHER PUBLICATIONS

Hattori et al., Next-generation antibodies for post-translational modifications, Current Opinion in Structural Biology, 2018, 141-148 (Year: 2018).*
Mihaylova et al., Cell, 145(4):607-621 (2011).
Montellier et al, Bioessays, 34:187-193 (2011).
Moriniere et al., Nature, 461:664-668 (2009).
Mukherjee et al.; Trends in Biochemical Sciences, 32(5):210-216 (2007).
Olsen et al., Science Signaling, 3(ra3):1-20 (2010).
Peng et al., Molecular & Cellular Proteomics, 10(12):1-12 (2011).
Perche et al., Curr. Biol., 10:1531-1534 (2010).
Preuveneers et al., Biochem, J., 133:133-157 (1973).
Reusch et al., FEBS Letters, 527:319-322 (2002).
Reynard et al., J. Cell Science, 122:4239-4248 (2009).
Rohwerder et al., Microbial Cell Factories, 9(13):1-10 (2010).
Ruepp et al., Nucleic Acids Research 36:D646-650 (2008).
Sakabe et al., PNAS, 107(46):19915-19920 (2010).
Schwartz et al., Nature Biotechnology 23(11):1391-1398 (2005).
Shannon et al., Genome Research, 13:2498-2504 (2003).
Shechter et al., Nature Protocols, 2(6):1445-1457 (2007).
Shimazu et al., Science 339(6116):211-214 (2013).
Taggart et al., J. Biol. Chem., 280(29):26649-26652 (2005).
Tan et al., Cell, 146:1016-1028 (2011).
Wang et al., Proteomics, 11(10):2019-2026 (2011).
Wang et al., Theory and Application of Medical Experimental Technology, p. 176 (2004).
Wellen et al., Science, 324(5930):1076-1080 (2009).
Whitfield et al., Mol. Biol. Cell, 13:1977-2000 (2002).
Wisniewski et al., Nucleic Acids Research, 36(2):570-577 (2008).
Xie et al., Molecular & Cellular Proteomics, 11(5):100-107 (2012).
Aksnes et al., Trends in Biochemical Sciences, 41(9):746-760 (2016).
Allis et al., Proc. Natl. Acad. Sci. USA, 82:8048-8052 (1985).
Ashburner et al., Nature Genetics, 25(1):25-29 (2000).
Bader et al., BMC Bioinformatics, 4(2):1-27 (2003),.
Benjamin et al., Journal of the Royal Statistical Society. Series B (Methodological), 57(1):289-300 (1995).
Berger, Nature, 447:407-412 ( 2007).
Bough et al., Epilepsia, 48(1):43-58 (2007).
Cahill et al., Trans. Am. Clin. Climatol. Assoc., 114:149-163 (2003).
Chen et al., PLoS Genetics, 6(9):1-18, e1001093 (2010).
Chen et al., Molecular & Cellular Proteomics, 6(5):812-9 (2007).
Chen et al., Proc. Natl. Acad. Sci. USA, 106(3):761-766 (2009).
Chen et al., Molecular & Cellular Proteomics, 11(10):1048-1062 (2012).
Chi et al., Nat. Rev. Cancer, 10(7):457-469 (2010).
Chinese Office Action for Chinese Application No. 201410406258.1, dated Nov. 14, 2018, with translation—23 pages.
Choudhary et al., Science, 325:834-840 (2009).
Colaert et al. Nat. Methods, 6(11):786-787 (2009).

(Continued)

*Primary Examiner* — Andrea S Grossman
(74) *Attorney, Agent, or Firm* — RatnerPrestia

(57) ABSTRACT

The invention provides an isolated peptide comprising a lysine 3-hydroxybutyrylation site, a lysine 3-hydroxybutyrylation specific affinity reagent that specifically binds to the peptide, and a method for detecting protein lysine 3-hydroxybutyrylation in a sample using the reagent.

6 Claims, 5 Drawing Sheets

Specification includes a Sequence Listing.

(56) References Cited

OTHER PUBLICATIONS

Cox et al., J. Proteome Res., 10:1794-1805 (2011).
Crooks et al., Genome Research, 14:1188-1190 (2004).
Dai et al., Nature Chemical Biology, 10:365-73 (2014).
Drogaris et al., Sci. Rep., 2(220):1-12 (2012).
Du et al., Science, 334(6057):806-809 (2011).
Finn et al., J. Biol. Chem., 280(27):25864-25870 (2005).
Finn et al., Nucleic Acids Research, 36:D281-288 (2008).
Finn et al., Nucleic Acids Research, 42:D222-D230 (2014).
Freeman et al., Epilepsy Res., 68:145-180 (2006).
Freitas et al., J. Cell Biochem, 92(4):691-700 (2004).
Gao et al., Journal of Chromatography B, 853:303-313 (2007).
Gaucher et al., The EMBO Journal, 31(19):3809-3820 (2012).
Guarente, Cell Metabolism, 14:151-153 (2011).
Guarente, Cold Spring Harb. Symp. Quant. Biol., 76:81-90 (2011).
Haberland et al., Nat. Rev. Genet., 10(1):32-42 (2009).
Heintzman et al., Nat. Genet., 39(3):311-318 (2007).
Hornbeck et al., Nucleic Acids Research, 40:D261-270 (2012).
Jensen et al., Nucleic Acids Research, 37:D412-416 (2009).
Kanehisa et al., Nucleic Acids Research, 28(1):27-30 (2000).
Kashiwaya et al., Proc. Natl. Acad. Sci. USA, 97(10):5440-5444 (2000).
Katada et al., Cell, 148:24-28 (2012).
Kim et al., Trends in Biochemical Sciences, 36(4):211-220 (2011).
Kristensen, Beilstein J. Org. Chem., 11:446-468 (2015).
Kumps et al., Clin. Chem, 48(5):708-717 (2002).
Lim et al., PLoS One, 6(9):1-10, e24620 (2011).
Lin et al., ACS Chem. Biol., 7:947-960 (2012).
Linares, Retrieved from https://edoc.ub.uni-muenchen.de/19313/Moura_Linares_Elisangela.pdf on Jul. 25, 2016, 148 pages (2013).
Long Liu et al., Arthritis Research & Therapy, 14(R25):1-14 (2012).
Lu et al., Cell Metab. 16(1):9-17 (2012).
Martin et al., Nat. Rev. Mol. Cell Biol., 6:838-849 (2005).
McNally et al., J. Neurochem, 121(1):28-35 (2012).
Maxwell et al., Nature, 399:271-275 (1999).
Martinez-Outschoorn et al., Cell Cycle, 10(8):1271-1286 (2011).
Mietton et al., Mol. Cell. Biol., 29(1):150-156 (2009).
Non Final Office Action for U.S. Appl. No. 16/251,822, dated Nov. 10, 2020, 28 pages.
Lee, et al., "Antibody Production with Synthetic Peptides", Methods Mol. Biol., 2016, vol. 1474, pp. 25-47.

* cited by examiner

FIG. 2
Replacement Sheet
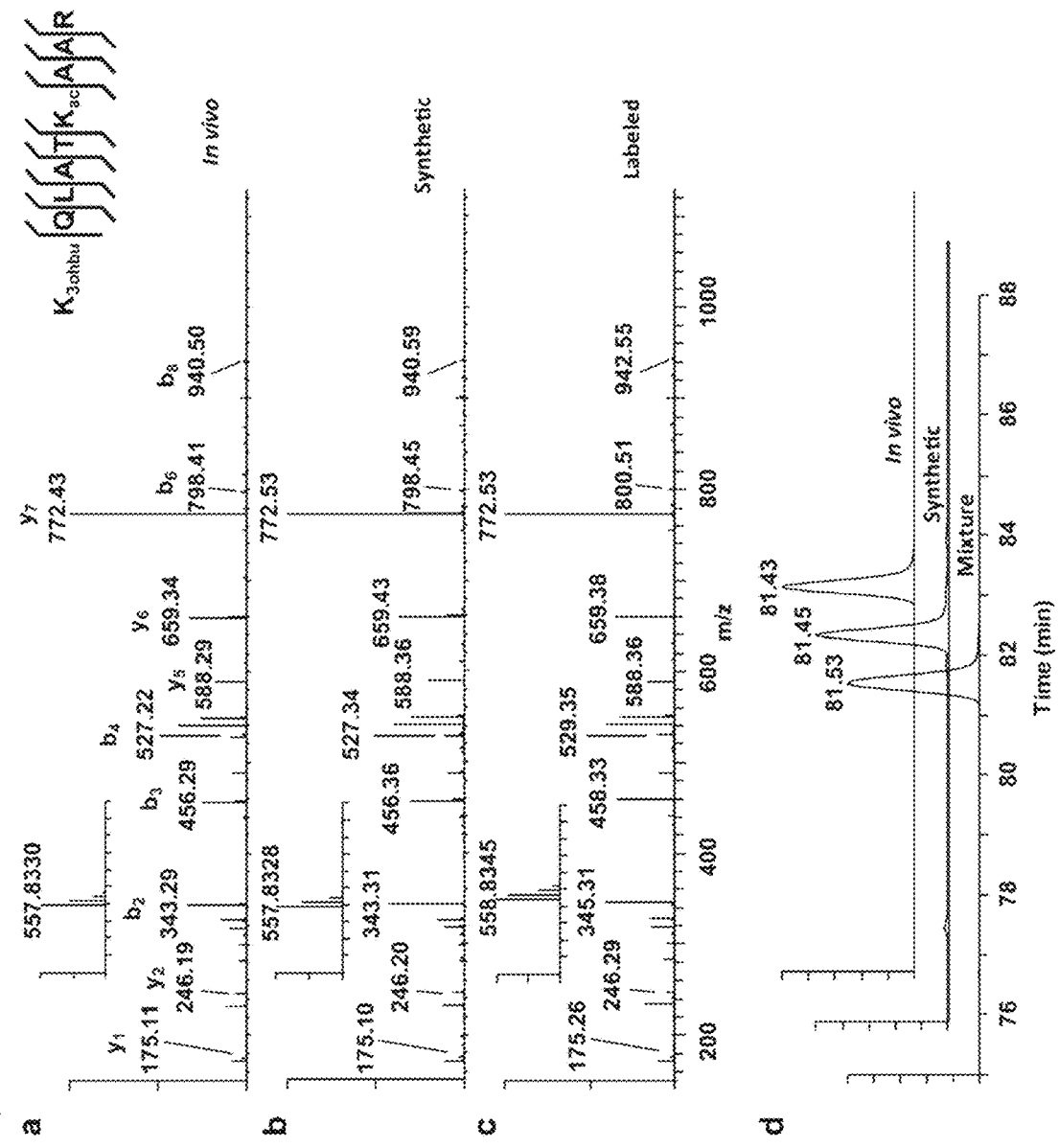

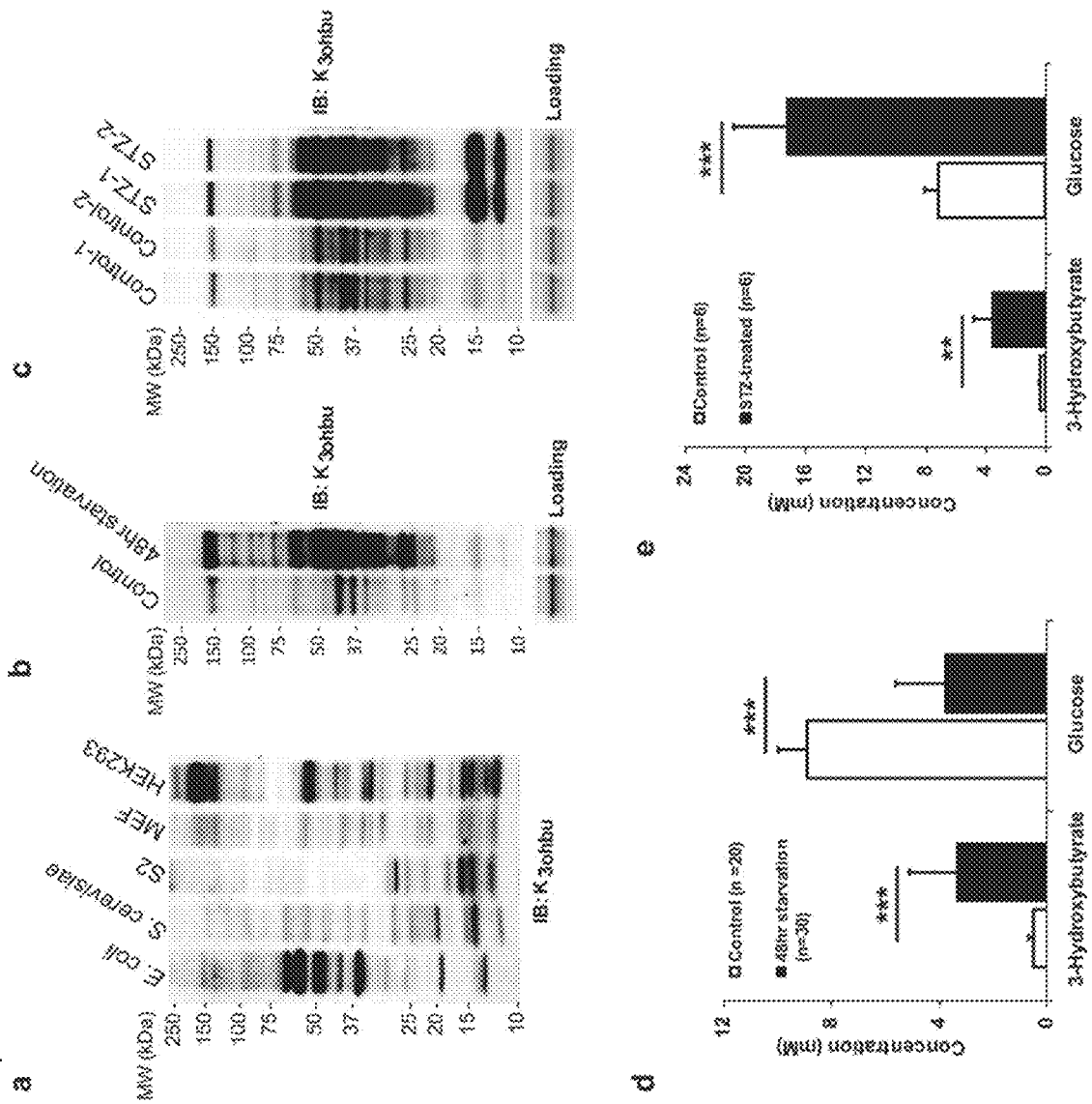
FIG. 3
Replacement Sheet

FIG. 4
Replacement Sheet
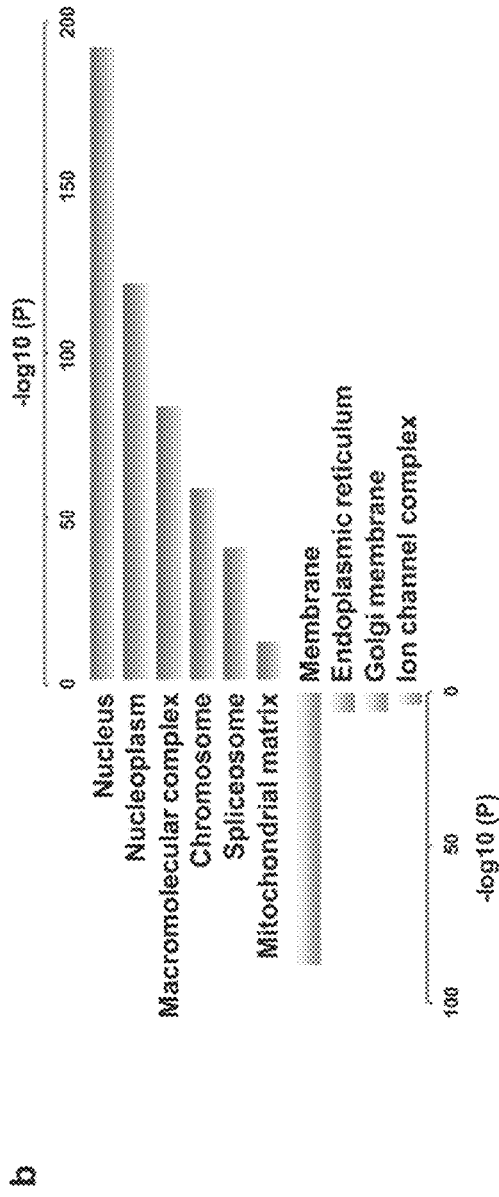
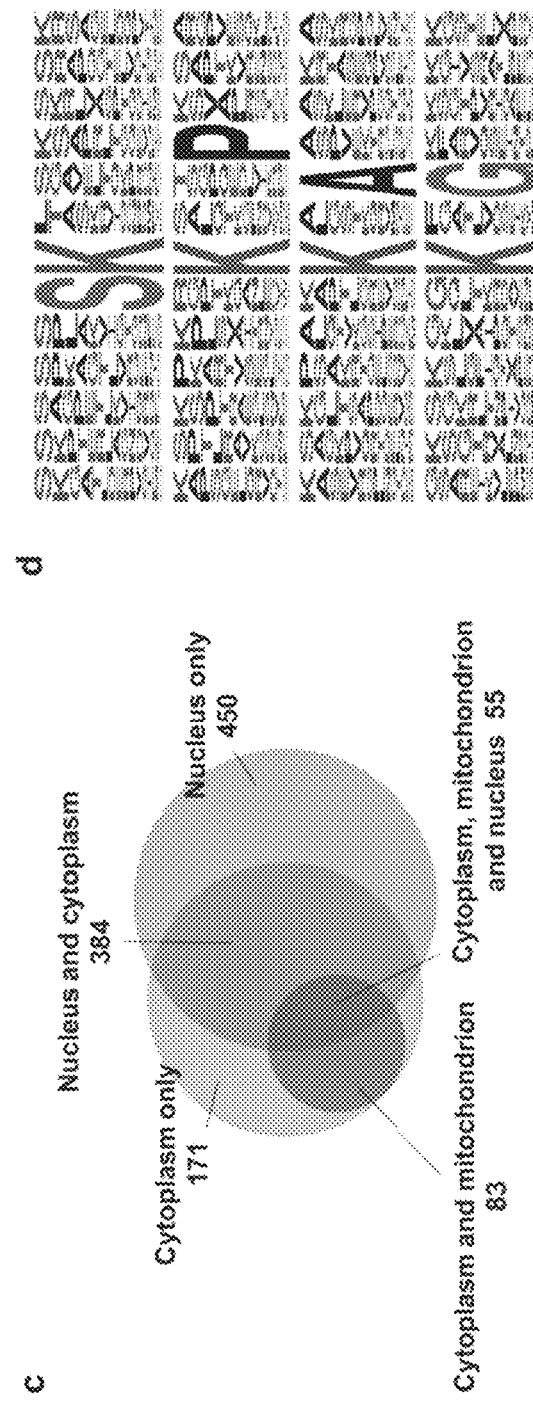

REAGENTS AND METHODS FOR DETECTING PROTEIN LYSINE 3-HYDROXYBUTYRYLATION

CROSS-REFERENCE TO RELATED APPLICATION

This application is a divisional application of U.S. patent application Ser. No. 14/121,311, filed on Aug. 18, 2014 and is related to and claims the benefit of U.S. Provisional Application No. 61/866,725, entitled "REAGENTS AND METHODS FOR DETECTING PROTEIN LYSINE 3-HYDROXYBUTYRYLATION" filed Aug. 16, 2013, the contents of which are incorporated herein by reference in their entireties for all purposes.

REFERENCE TO U.S. GOVERNMENT SUPPORT

This work is supported by a grant from National Institutes of Health under Award Numbers CA126832. The United States has certain rights in the invention.

The Sequence Listing for this application is labeled "Sequence Listing," which was created on Mar. 31, 2020 and is 70.7 KB. The entire content of the Sequence Listing is incorporated herein by reference in its entirety.

FIELD OF THE INVENTION

This invention relates to reagents and methods for detecting proteins having post-translational modifications. More particularly, it relates to peptides comprising a 3-hydroxybutyrylated lysine, and their uses to develop reagents and methods useful for detecting protein lysine 3-hydroxybutyrylation.

BACKGROUND OF THE INVENTION

Emerging lines of evidence suggest that cellular metabolism is associated with chromatin structure and epigenetic programming. Enzymes regulating histone protein post-translational modifications (PTMs), or histone marks, use high energy co-substrates, such as acetyl-CoA and S-adenosylmethionine, for protein PTM reactions. In response to the extracellular environment, the intracellular concentrations of these cofactors may change, in turn affecting the status of histone marks. In addition, the activity of histone PTM enzymes can be modulated by cellular metabolites, such as NAD and 2-hydroxyglutarate.

Histone PTMs, such as lysine acetylation, are also abundantly present in other proteins, and have diverse DNA-independent functions, including effects on metabolism[11]. The recent discovery of new histone marks and the high complexity of cellular metabolisms imply the possibility of undescribed histone marks and PTM pathways which are modulated by metabolic signals.

3-Hydroxybutyrate is a component of ketone bodies and an important energy source for tissues during starvation. It regulates gene expression and exhibits neuroprotective effects in diverse chronic neurological diseases. However, the molecular mechanisms underlying these effects remain unclear.

There remains a need for developing reagents and methods useful for detecting post-translational modifications of histones or nonhistone proteins linked to various diseases and disorders.

SUMMARY OF THE INVENTION

The present invention relates to the use of peptides comprising a 3-hydroxybutyrylated lysine ($K_{3ohbu}$) to develop reagents and methods for detecting protein lysine 3-hydroxybutyrylation, especially site specific lysine 3-hydroxybutyrylation.

An isolated peptide comprising a 3-hydroxybutyrylated lysine is provided. The isolated peptide may be derived from a histone protein or a fragment thereof. The histone protein may be derived from an organism selected from the group consisting of human, mouse, *S. cerevisiae*, *Tetrahymena thermophila*, *D. melanogaster*, and *C. elegans*. The isolated peptide may comprise an amino acid sequence having at least 70% identity to an amino acid sequence selected from the group consisting of SEQ ID NOs: 29-102. The isolated peptide may comprise an amino acid sequence selected from SEQ ID NOs: 29-102. The isolated peptide may comprise at least 2 amino acid residues on each of the N-terminal and C-terminal sides of the 3-hydroxybutyrylated lysine.

An isolated lysine 3-hydroxybutyrylation specific affinity reagent is also provided. It is capable of binding specifically to a peptide comprising a 3-hydroxybutyrylated lysine. The peptide may comprise an amino acid sequence selected from SEQ ID NOs: 29-102. The binding may be dependent on the presence of the 3-hydroxybutyrylated lysine but not a surrounding peptide sequence thereof in the peptide. The binding may be dependent on the presence of the 3-hydroxybutyrylated lysine and a surrounding peptide sequence thereof in the peptide. The lysine 3-hydroxybutyrylation specific affinity reagent may be a protein or an antibody.

A method for producing a lysine 3-hydroxybutyrylation specific affinity reagent that is a protein is provided. The method comprises screening a protein library using a peptide comprising a 3-hydroxybutyrylated lysine and at least two amino acid residues on each of the N-terminal and C-terminal sides of the 3-hydroxybutyrylated lysine. The protein library may be selected from the group consisting of a phage display library, a yeast display library, a bacterial display library, and a ribosome display library.

A method for producing a lysine 3-hydroxybutyrylation specific affinity reagent that is an antibody is also provided. The method comprises immunizing a host with a peptide comprising a 3-hydroxybutyrylated lysine and at least two amino acid residues on each of the N-terminal and C-terminal sides of the 3-hydroxybutyrylated lysine.

A method for detecting a 3-hydroxybutyrylated lysine in a protein or a fragment thereof is provided. The method comprises contacting the protein or a fragment thereof with the isolated lysine 3-hydroxybutyrylation specific affinity reagent capable of binding specifically to a peptide comprising a 3-hydroxybutyrylated lysine. The lysine 3-hydroxybutyrylation specific affinity reagent and the protein or a fragment thereof forms a binding complex. The method further comprises detecting the binding complex. The presence of the binding complex indicates the presence of a 3-hydroxybutyrylated lysine in the protein or a fragment thereof. In this method, the lysine 3-hydroxybutyrylation specific affinity reagent may be a protein or an antibody.

A method for determining the level of protein lysine 3-hydroxybutyrylation in a sample is provided. The method comprises detecting a 3-hydroxybutyrylated lysine in the sample.

A kit for detecting a 3-hydroxybutyrylated lysine in a protein of a fragment thereof is provided. The kit comprises an isolated lysine 3-hydroxybutyrylation specific affinity reagent capable of binding specifically to a peptide comprising a 3-hydroxybutyrylated lysine.

A kit for isolating a peptide containing a 3-hydroxybutyrylated lysine is also provided. The kit comprises an isolated lysine 3-hydroxybutyrylation specific affinity reagent capable of binding specifically to a peptide comprising a 3-hydroxybutyrylated lysine.

BRIEF DESCRIPTION OF THE DRAWINGS

FIG. 2 shows identification and confirmation of a Lys 3-hydroxybutyrylated peptide. (a) MS/MS spectrum of a tryptic peptide derived from HEK293 core histones, KQLATK$_{ac}$AAR (SEQ ID NO: 29), where K$_{ac}$ indicates acetyllysine. The peptide has a mass shift of +86.0276 Da at its Lys 1 residue. (b) MS/MS spectrum of the synthetic peptide K$_{3ohbu}$QLATK$_{ac}$AAR (SEQ ID NO: 29), where K$_{3ohbu}$ indicates 3-hydroxybutyryllysine. (c) MS/MS spectrum of K$_{3ohbu\ (heavy)}$QLATK$_{ac}$AAR (SEQ ID NO: 29) identified from (R/S)-3-hydroxybutyrate-[2,4-$^{13}$C2] treated HEK293 cells. The insets show the mass-to-charge ratios (m/z) of the doubly charged precursor peptide ions. (d) Reconstructed ion chromatograms from HPLC/MS/MS analyses of the in vivo-derived K$_{+86.0276}$QLATK$_{ac}$AAR (SEQ ID NO: 29) peptide, its synthetic K$_{3ohbu}$ counterpart, and their mixture, showing co-elution of the two peptides.

FIG. 3 shows detection of Lys 3-hydroxybutyrylation in cells. Western blot analysis, using a pan anti-K$_{3ohbu}$ antibody, of (a) whole cell lysates from E. coli, S. cerevisiae, D. melanogaster S2 cells, MEF cells, and HEK293 cells, (b) liver whole-cell lysates from either control or starved (48 hours) male mice, and (c) liver whole-cell lysates from either control or STZ-treated female mice. Uniformity of sample loading was checked by staining the membrane with Ponceau S after protein transfer but prior to incubation with antibody. Concentrations of blood glucose and 3-hydroxybutyrate in (d) starved and (e) STZ-treated mice relative to controls. P<0.01, *P<0.001, Error bars show SD.

DETAILED DESCRIPTION OF THE INVENTION

Figure 1:
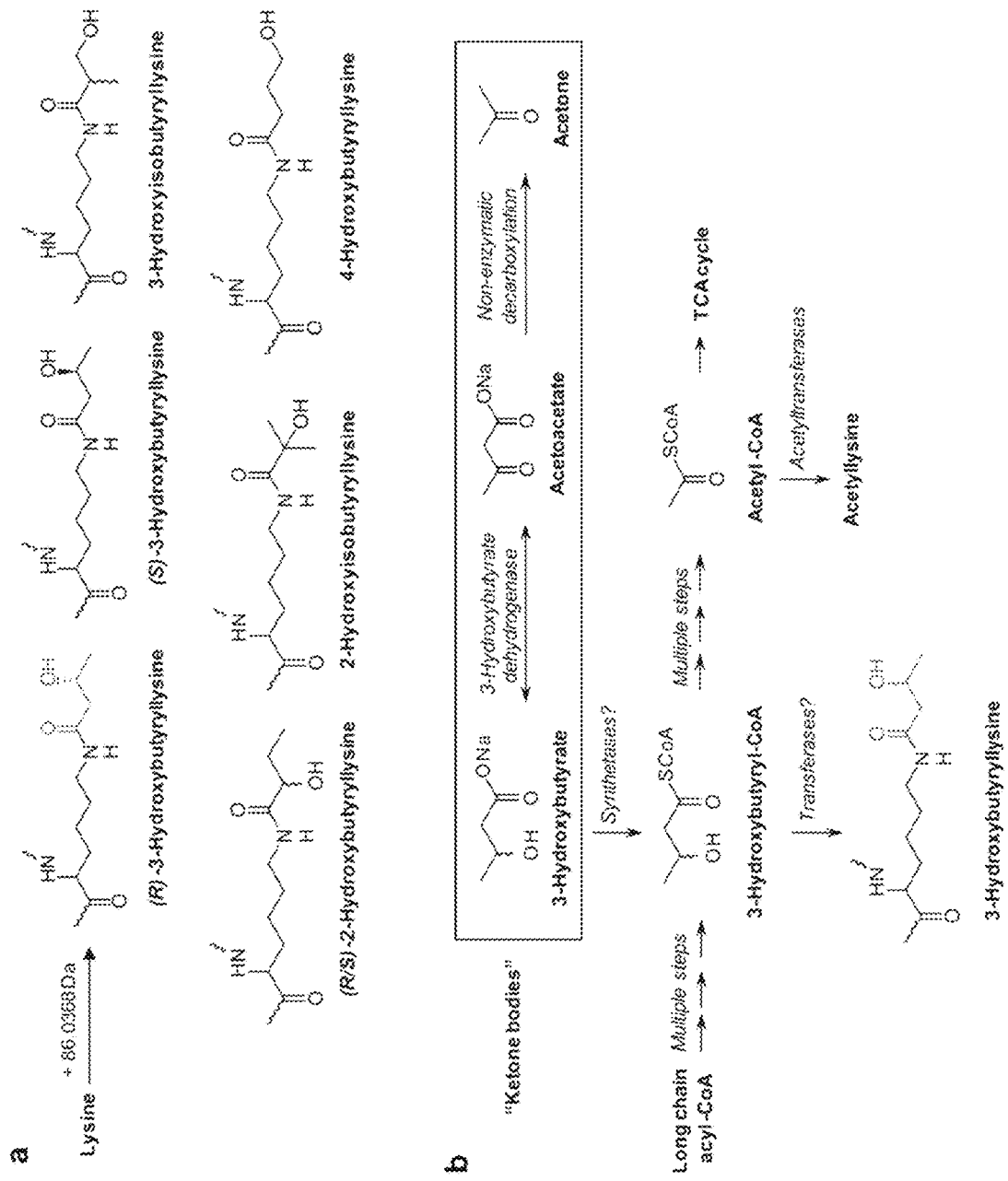
FIG. 1 shows chemical structures of 3-hydroxybutyryl lysine isomers and biosynthetic pathways. (a) Each isomer causes a predicted mass shift of +86.0368 Da. (b) Biosynthetic pathways for 3-hydroxybutyrate and 3-hydroxybutyryl-CoA. Also listed are the three ketone bodies: 3-hydroxybutyrate, acetoacetate, and acetone.

The present invention is based on the discovery of a new type of histone marks, lysine 3-hydroxybutyrylation. In particular, lysine 3-hydroxybutyrylation (K$_{3ohbu}$) have been identified and verified as a new, evolutionarily conserved protein post-translational modification (PTM). 3-Hydroxybutyrate can label and stimulate K$_{3ohbu}$, presumably via conversion of 3-hydroxybutyrate to 3-hydroxybutyryl-CoA. K$_{3ohbu}$ is a pervasive and dynamic PTM that is influenced by physiological conditions and cell status. For example, 45 non-redundant K$_{3ohbu}$ sites in histones of HEK293 and mouse liver cells, and 3008 K$_{3ohbu}$ sites in HEK293 cells have been identified. The present invention provide evidence to link ketone metabolism to chromatin structure, and opens up a new avenue to study the pharmacological functions and diverse roles of 3-hydroxybutyrate in pathophysiological processes.

The term "peptide" used herein refers to a linear chain of two or more amino acids linked by peptide bonds. A peptide may have about 2, 3, 4, 5, 6, 7, 8, 9, 10, 11, 12, 13, 14, 15, 16, 17, 18, 19, 20, 25, 30, 40, 50, 100, 200 or more amino acids. The amino acids of a peptide may be modified, deleted, added or substituted. A peptide may be obtained using conventional techniques known in the art. For example, a peptide may be synthesized or obtained from a native or recombinant protein by enzymatic digestion.

The term "polypeptide" used herein refers to a peptide having at least 4 amino acids, preferably at least about 20 amino acids, regardless of post-translational modification. The term "protein" used herein refers to a biological molecule consisting of one or more polypeptides, regardless of post-translational modification. Each polypeptide in a protein may be a subunit. The polypeptide or protein may be in a native or modified form, and may exhibit a biological function or characteristics.

Where a protein is a single polypeptide, the terms "protein" and "polypeptide" are used herein interchangeably. A fragment of a polypeptide or protein refers to a portion of the polypeptide or protein having an amino acid sequence that is the same as a part, but not all, of the amino acid sequence of the polypeptide or protein. Preferably, a fragment of a polypeptide or protein exhibits a biological function or characteristics identical or similar to that of the polypeptide or protein.

The term "derived from" used herein refers to the origin or source from which a biological molecule is obtained, and may include naturally occurring, recombinant, unpurified or purified molecules. A biological molecule such as a peptide (e.g., a polypeptide or protein) may be derived from an original molecule, becoming identical to the original molecule or a variant of the original molecule. For example, a peptide derived from an original peptide may have an amino acid sequence identical or similar to the amino acid sequence of its original peptide, with at least one amino acid modified, deleted, inserted, or substituted. A derived peptide may have an amino acid sequence at least about 5%, 10%, 20%, 30%, 40%, 50%, 60%, 70%, 80%, 90%, 95%, 99% or 100%, preferably at least about 50%, more preferably at least about 80%, most preferably at least about 90%, identical to the amino acid sequence of its original peptide, regardless of post-translational modification. Preferably, a derived biological molecule (e.g., a peptide) may exhibit a biological function or characteristics identical or similar to that of the original biological molecule.

The term "antibody" used herein includes whole antibodies, and antigen binding fragments (or antigen-binding portions) and single chains thereof. A whole antibody can be either one of the two types. The first type refers to a glycoprotein typically having two heavy chains and two light chains, and includes an antigen binding portion. For example, the antibody may be a polyclonal or monoclonal antibody. The term "antigen binding portion" of an antibody used herein refers to one or more fragments of the antibody that retain the ability of specifically binding to an antigen. The second type refers to a heavy-chain antibody occurring in camelids that is also called Nanobody. The term "single-chain variable fragment" of an antibody used herein refers to a fusion protein of the variable regions of the heavy and light chains of the antibody, connected with a short linker peptide, for example, of about 20-25 amino acids, that retains the ability of specifically binding to an antigen.

An isolated peptide comprising a 3-hydroxybutyrylated lysine is provided. The term "3-hydroxybutyrylated lysine" used herein refers to a lysine residue that is modified by a 3-hydroxybutyryl group at its epsilon-amine group. It may be in R-form or S-form, preferably R-form. The term "lysine 3-hydroxybutyrylation site" used herein refers to a lysine residue in a peptide, polypeptide or protein that may be 3-hydroxybutyrylated on the epsilon-amine group of the lysine residue. The term "lysine 3-hydroxybutyrylation" used herein refers to 3-hydroxysobutyrylation on the epsilon-amine group of a lysine residue that generates a 3-hydroxysobutyryl lysine residue or 3-hydroxybutyrylated lysine.

The peptide of the present invention may have at least about 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The peptide may have about 3-25 amino acids, preferably 5-20 amino acids, more preferably 6-14 amino acids.

The peptide of the present invention may be prepared using conventional techniques known in the art. The peptide may be derived from a protein, for example, a histone protein, or a fragment thereof, having a lysine 3-hydroxybutyrylation site. The histone protein may be derived from a eukaryotic cell. Examples of a eukaryotic cell include cells from a yeast (e.g., S. cerevisiae), an C. elegans, a Drosophila (e.g., D. melanogaster (S2)), a Tetrahymena (e.g., Tetrahymena thermophila), a mouse (e.g., M. musculus (MEF)), or a human. Preferably, the eukaryotic cell is a mammalian cell, for example, a human, primate, mouse, rat, horse, cow, pig, sheep, goat, chicken, dog or cat cell. More preferably, the eukaryotic cell is a human cell.

The histone protein may be a histone linker protein or a histone core protein. A histone linker protein may be selected from the members of the H1 family, including the H1F subfamily (e.g., H1F0, H1FNT, H1FOO, and H1FX) and the H1H1 subfamily (e.g., HIST1H1A, HIST1H1B, HIST1H1C, HIST1H1D, HIST1H1E and HIST1H1T). A histone core protein may a member of the H2A, H2B, H3 or H4 family. A histone core protein in the H2A family may be a member of the H2AF subfamily (e.g., H2AFB1, H2AFB2, H2AFB3, H2AFJ, H2AFV, H2AFX, H2AFY, H2AFY2, and H2AFZ), the H2A1 subfamily (e.g., HIST1H2AA, HIST1H2AB, HIST1H2AC, HIST1H2AD, HIST1H2AE, HIST1H2AG, HIST1H2AH, HIST1H2AI, HIST1H2A3, HIST1H2AK, HIST1H2AL, and HIST1H2AM), or the H2A2 subfamily (e.g., HIST2H2AA3, HIST2H2AA4, HIST2H2AB, and HIST2H2AC). A histone core protein in the H2B family may be a member of the H2BF subfamily (e.g., H2BFM and H2BFWT), the H2B1 subfamily (e.g., HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, and HIST1H2BO), or the H2B2 subfamily (e.g., HIST2H2BE and HIST2H2BF). A histone core protein in the H3 family may be a member of the H3A1 subfamily (e.g., HIST1H3A, HIST1H3B, HIST1H3C, HIST1H3D, HIST1H3E, HIST1H3F, HIST1H3G, HIST1H3H, HIST1H3I, and HIST1H3J), the H3A2 subfamily (e.g., HIST2H3A, HIST2H3C, and HIST2H3D), or the H3A3 subfamily (e.g., HIST3H3), the H3A3 subfamily (e.g., H3F3A, H3F3B, and H3F3C). A histone core protein in the H4 family may be a member of the H41 subfamily (e.g., HIST1H4A, HIST1H4B, HIST1H4C, HIST1H4D, HIST1H4E, HIST1H4F, HIST1H4G, HIST1H4H, HIST1H4I, HIST1H4J, HIST1H4K, and HIST1H4L), or the H44 subfamily (e.g., HIST4H4).

The protein and gene sequences of histone proteins in various species are known in the art. For example, histone protein sequences of human, mouse, S. cerevisiae, Tetrahymena, D. melanogaster, and C. elegans can be found in GenBank database Accession Nos. GenBank database Accession No. P16403 (H1.2_HUMAN) (SEQ ID NO: 1), P0C0S8 (H2A.1_HUMAN) (SEQ ID NO: 2), P33778 (H2B.1B_HUMAN) (SEQ ID NO: 3), P84243 (H33_HUMAN) (SEQ ID NO: 4), and P62805 (H4_HUMAN) (SEQ ID NO: 5); P15864 (H12_MOUSE) (SEQ ID NO: 6), P22752 (H2A1_MOUSE) (SEQ ID NO: 7), P10853 (H2B1F/G/L_MOUSE) (SEQ ID NO: 8), P84244 (H33_MOUSE) (SEQ ID NO: 9), and P62806 (H4_MOUSE) (SEQ ID NO: 10); P04911 (H2A.1_S. cerevisiae) (SEQ ID NO: 11), P02294 (H2B.2_S. cerevisiae) (SEQ ID NO: 12), P61830 (H3_S. cerevisiae) (SEQ ID NO: 13), and P02309 (H4_S. cerevisiae) (SEQ ID NO: 14); P35065 (H2A.1_Tetrahymena thermophila) (SEQ ID NO: 15), P08993 (H2B.1_Tetrahymena thermophila) (SEQ ID NO: 16), I7LUZ3 (H3_Tetrahymena thermophila) (SEQ ID NO: 17), and P69152 (H4_Tetrahymena thermophila) (SEQ ID NO: 18); P02255 (H1_D. melanogaster) (SEQ ID NO: 19), P08985 (H2A.V_D. melanogaster) (SEQ ID NO: 20), P02283 (H2B_D. melanogaster) (SEQ ID NO: 21), P02299 (H3) (SEQ ID NO: 22), and P84040 (H4_D. melanogaster) (SEQ ID NO: 23); P10771 (H1.1_c. elegans) (SEQ ID NO: 24), P09855 (H2A_c. elegans) (SEQ ID NO: 25), P04255 (H2B.1_c. elegans) (SEQ ID NO: 26), P08898 (H3_c. elegans) (SEQ ID NO: 27), and P62784 (H4_c. elegans) (SEQ ID NO: 28).

A fragment of a histone protein may have an amino acid sequence that is the same as a part, not all, of the amino acid sequence of the histone protein comprising at least one lysine 3-hydroxybutyrylation site. The histone protein fragment may have at least about 1, 2, 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The histone fragment may have about 3-25 contiguous amino acids, preferably about 5-20 contiguous amino acids, more preferably about 6-14 contiguous amino acids, of the histone protein covering at least one lysine 3-hydroxybutyrylation site in the histone protein.

The histone protein or fragment may have a 3-hydroxybutyrylated lysine at a lysine 3-hydroxybutyrylation site. The lysine 3-hydroxybutyrylation site may be any one of the lysine 3-hydroxybutyrylation sites in exemplary histone proteins of human (Table 1) and mouse (Table 2).

A histone protein may be obtained from a biological sample or prepared using recombinant techniques. A histone protein fragment may be prepared by recombinant techniques, or by digesting the histone protein with an enzyme (e.g., trypsin). The lysine 3-hydroxybutyrylation site in the histone protein or fragment may be lysine 3-hydroxybutyrylated naturally or artificially. The presence of a 3-hydroxybutyrylated lysine may be confirmed by using conventional techniques known in the art, for example, mass spectrometry.

The peptide of the present invention may comprise an amino acid sequence having at least about 70%, 80%, 90%, 95% or 99%, preferably at least about 90%, more preferably 100%, identity to an amino acid sequence selected from the group consisting of SEQ ID NOs: 29-102. The peptide may encompass any lysine 3-hydroxybutyrylation site with or without its surrounding sequences from a histone proteins. The peptide may comprise more than one 3-hydroxybutyrylated lysine. The peptide may also comprise a protein post-translational modification other than 3-hydroxybutyrylated lysine, such as acetylated lysine or methylated lysine. The peptides may further comprise at least about 1, 2, 3, 4, 5, 6, 7, 8, 9, 10 or more residues on either or both of N-terminal and C-terminal sides of the 3-hydroxybutyrylated lysine. Preferably, the peptide may comprise at least 2 amino acid residues on each of the N-terminal and C-terminal side of the 3-hydroxybutyrylated lysine. Exemplary peptides of the present invention are shown in Tables 1 and 2.

An isolated lysine 3-hydroxybutyrylation specific affinity reagent is also provided. The term "lysine 3-hydroxybutyrylation specific affinity reagent" used herein refers to a molecule that is capable of binding to a peptide, polypeptide or protein having a lysine 3-hydroxybutyrylation site, which may be a histone protein or a peptide of the present invention. The lysine 3-hydroxybutyrylation specific affinity reagent may be a protein, for example, an antibody. The lysine 3-hydroxybutyrylation site may be any lysine 3-hydroxybutyrylation site in any histone protein from any species. Examples of the lysine 3-hydroxybutyrylation sites include those in human (Table 1) and mouse (Table 2), and homologous lysine sites in corresponding eukaryotic histone proteins.

In some embodiments, the lysine 3-hydroxybutyrylation specific affinity reagent binds a peptide, polypeptide or protein having a lysine 3-hydroxybutyrylation site that is 3-hydroxybutyrylated, either in R-form or S-form, preferably in R-form, having an affinity that is at least about 10, 50, 100, 500, 1000 or 5000 times higher than that for its counterpart when the site is not 3-hydroxybutyrylated.

In other embodiments, the lysine 3-hydroxybutyrylation specific affinity reagent binds a peptide, polypeptide or protein having a lysine 3-hydroxybutyrylation site that is not 3-hydroxybutyrylated, having an affinity that is at least about 10, 50, 100, 500, 1000 or 5000 times higher than that for its counterpart when the site is 3-hydroxybutyrylated, either in R-form or S-form, preferably in R-form. The lysine 3-hydroxybutyrylation specific affinity reagent may be a peptide, polypeptide or protein, which may be an antibody. Preferably, the peptide is a peptide of the present invention.

The lysine 3-hydroxybutyrylation specific affinity reagent may be site specific, i.e., the binding is dependent on the presence of the 3-hydroxybutyrylated lysine, either in R-form or S-form, preferably in R-form, and its surrounding peptide sequence. The surrounding peptide sequence may include at least about 1, 2, 3, 4, 5, 6, 7, 8, 9, 10 or more residues on either or both of N-terminal and C-terminal sides of the 3-hydroxybutyrylated lysine. For example, the binding depends on the presence of the 3-hydroxybutyrylated lysine and at least 2 amino acid residues on each of the N-terminal and C-terminal side of the 3-hydroxybutyrylated lysine.

The lysine 3-hydroxybutyrylation specific affinity reagent may not be site specific, i.e., the binding is dependent on the presence of the 3-hydroxybutyrylated lysine but not its surrounding peptide sequence. One example is an anti-lysine-3-hydroxybutyrylation pan antibody.

A method for producing the lysine 3-hydroxybutyrylation specific affinity reagent of the present invention is further provided.

Where the lysine 3-hydroxybutyrylation specific affinity reagent is a protein, the protein may be produced by screening a protein library (also known as a display library or a degenerated protein library) using the peptide of the present invention. The peptide may have at least two amino acid residues one each of the N-terminal and C-terminal sides of the 3-hydroxybutyrylated lysine. The protein library may consist of many degenerated protein sequences, which may comprise two regions: one or more fixed peptide sequence regions and a plurality of degenerated amino acid sequences. The protein library may be a phage protein library, a yeast protein library, bacterial protein library, ribosome protein library, or other synthetic protein library comprising peptides having randomized amino acid sequences.

Where the lysine 3-hydroxybutyrylation specific affinity reagent is an antibody, the antibody may be produced by different methods known in the art. For example, the production method may comprise immunizing a host with an antigenic peptide to produce the antibody. The method may further comprise collecting antisera from the host. The host may be a mammal suitable for producing antibodies. For example, the host may be a mouse, rabbit, goat, Camelidae family animal (such as Lama and camel), or cartilaginous fishes. Dependent on the host used, the generated antibody can contain either two chains (a heavy chain and a light chain) or one chain (or heavy chain-only antibody occurring in camelids) that is also called Nanobody.

The antigenic peptide may be derived from a histone protein or a fragment thereof comprising a lysine 3-hydroxybutyrylation site, which may be 3-hydroxybutyrylated or not. The antigenic peptide may comprise a peptide of the present invention. Examples of antigenic peptides having 3-hydroxybutyrylated lysine may comprise one or more of the peptides in Tables 1 and 2. Examples of antigenic peptides not having 3-hydroxybutyrylated lysine may have an amino acid sequence identical to those in Tables 1 and 2, except that the lysine 3-hydroxybutyrylation site is not 3-hydroxybutyrylated. The N-terminal or C-terminal end of any of these peptides may be extended by 1-20 residues.

The method may further comprise purifying the antibody from the antisera. The method may further comprise utilizing spleen cells from the host to generate a monoclonal antibody. In some embodiments, the antibody specifically binds to a histone protein or fragment having a lysine 3-hydroxybutyrylation site when the site is 3-hydroxybutyrylated, but not when the site is not 3-hydroxybutyrylated. In other embodiments, the antibody specifically binds to a histone protein or fragment having a lysine 3-hydroxybutyrylation site when the site is not 3-hydroxybutyrylated, but not when the site is 3-hydroxybutyrylated.

The method may further comprise deduce the antibody sequences by high-performance liquid chromatography (HPLC)-mass spectrometry analysis of the isolated antibodies and followed by protein sequence database search against all the possible IgG protein sequences (derived from cDNA sequences) from bone marrow (or B cells) of the immunized host. The IgG cDNA sequences can be obtained from conventional DNA sequencing technologies from IgG cDNAs that are generated by RT-PCR using the known art. The derived heavy- and light-chain variable regions (VH and VL) can be further paired (in case the IgG is from a two-chain antibodies from a host like mice or rabbit). Such a pairing is not necessary for those IgG derived from heavy chain-only antibody (or Nonabody) from Lama. The antibody can then be generated using the antibody sequence information using the known art.

A method for detecting a 3-hydroxybutyrylated lysine in a protein or its fragment is provided. The 3-hydroxybutyrylated lysine may be R-3-hydroxybutyrylated lysine or S-3-hydroxybutyrylated lysine, preferably R-3-hydroxybutyrylated lysine. The method comprises (a) contacting the protein or its fragment with a lysine 3-hydroxybutyrylation specific affinity reagent of the present invention to form a binding complex, and (b) detecting the binding complex. The presence of the binding complex indicates the presence of the 3-hydroxybutyrylated lysine in the protein or its fragment. The binding complex may be detected by using various conventional methods in the art. The protein may be a histone protein. The method may further comprise quantifying the amount of the binding complex. The amount of the binding complex may indicate the level of lysine 3-hydroxybutyrylation in the protein or its fragment.

For each detection method of the present invention, a kit is provided. The kit comprises a lysine 3-hydroxybutyrylation specific affinity reagent of the present invention. The lysine 3-hydroxybutyrylation specific affinity reagent may be R-lysine 3-hydroxybutyrylation specific affinity reagent or S-lysine 3-hydroxybutyrylation specific affinity reagent. The kit may further comprise an instruction directing how to carry out the method.

A fusion protein reporter is provided. The fusion protein reporter comprises a core flanked by a donor fluorescent moiety and an acceptor fluorescent moiety. The core includes a peptide, which comprises a lysine 3-hydroxybutyrylation site and a lysine 3-hydroxybutyrylation binding domain. The term "lysine 3-hydroxybutyrylation binding domain" used herein refers to a region in a protein sequence capable of specific binding to the lysine 3-hydroxybutyrylation site.

The fusion protein reporter of the present invention may be useful for determining protein lysine 3-hydroxybutyrylation level in a sample or screening for an agent that regulates protein lysine 3-hydroxybutyrylation by using the fluorescence resonance energy transfer (FRET). The FRET involves the transfer of photonic energy between fluorophores when in close proximity. Donor fluorescent moieties and acceptor fluorescent moieties suitable for FRET are known in the art. In the fusion protein reporter, the donor fluorescent moiety may be selected from the group consisting of cyan fluorescent protein (CFP), enhanced cyan fluorescent protein (ECFP), and A206K mutants thereof, and the acceptor fluorescent moiety may be selected from the group consisting of yellow fluorescent protein (YFP), enhanced yellow fluorescence protein (EYFP), Citrine, Venus, and A206K mutants thereof.

The peptide in the fusion protein reporter may comprise a peptide of the present invention. It may be derived from a histone protein or fragment comprising a lysine 3-hydroxybutyrylation site, where the histone protein or fragment may be 3-hydroxybutyrylated or not at the lysine 3-hydroxybutyrylation site.

The lysine 3-hydroxybutyrylation site may be located in the N-terminus, C-terminus or the core region of a histone protein. The N-terminus, C-terminus, and core regions of histone proteins (e.g., human or mouse H1.2, H2A, H2B, H3 or H4) are known in the art.

The fusion protein reporter may comprise one or more lysine 3-hydroxybutyrylation binding domains. A lysine 3-hydroxybutyrylation binding domain may be derived from a lysine 3-hydroxybutyrylation specific affinity reagent of the present invention.

In some embodiments, the lysine 3-hydroxybutyrylation site in the peptide is not 3-hydroxybutyrylated, and the lysine 3-hydroxybutyrylation binding domain specifically binds to the lysine 3-hydroxybutyrylation site when the site is 3-hydroxybutyrylated, but not when the sites is not 3-hydroxybutyrylated.

In other embodiments, the lysine 3-hydroxybutyrylation site in the peptide is 3-hydroxybutyrylated, and the lysine 3-hydroxybutyrylation binding domain specifically binds to the lysine 3-hydroxybutyrylation site when the peptide is not lysine 3-hydroxybutyrylated, but not when the site is 3-hydroxybutyrylated.

The lysine 3-hydroxybutyrylation site may be conjugated to the lysine 3-hydroxybutyrylation binding domain with a linker molecule. The linker molecule may be a peptide have any amino acid sequence, and may have about 1-50 amino acids, preferably 1-30 amino acids, more preferably 2-15. In some embodiments, the linker molecule may be -Gly-Gly-. The length and contents of a linker molecule may be adjusted to optimize potential fluorescence resonance energy transfer (FRET) between the donor fluorescent moiety and the acceptor fluorescent moiety when the lysine 3-hydroxybutyrylation site in the fusion protein reporter is 3-hydroxybutyrylated or not, and bound by the lysine 3-hydroxybutyrylating binding domain.

The fusion protein reporter may further comprise a targeting polypeptide. The targeting polypeptide may be selected from the group consisting of a receptor ligand, a nuclear localization sequence (NLS), a nuclear export signal (NES), a plasma membrane targeting signal, a histone binding protein, and a nuclear protein.

A method for determining the level of protein lysine 3-hydroxybutyrylation in a sample. The method comprises detecting a 3-hydroxybutyrylated lysine in the sample. The method may comprise (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein lysine 3-hydroxybutyrylation in the sample. The level of FRET may be increased or decreased after contacting.

A method for determining the level of protein de-lysine-3-hydroxybutyrylation in a sample is also provided. The method comprises (a) contacting the sample with a fusion protein reporter of the present invention, and (b) comparing the level of fluorescence resonance energy transfer (FRET) between the donor fluorescent moiety and the acceptor fluorescent moiety after contacting with that before contacting. The level of FRET indicates the level of protein de-lysine-3-hydroxybutyrylation in the sample. The level of FRET may be increased or decreased after contacting.

For the determination method of the present invention, a sample may be a biological sample (e.g., bodily fluid or serum). The biological sample may comprise a cell, a tissue biopsy, or a clinical fluid. The biological sample may be obtained from a subject (e.g., a mouse, rat, or human). The subject is healthy. The subject may have suffered from or may be predisposed to a protein lysine 3-hydroxybutyrylation or de-lysine-3-hydroxybutyrylation related disorder, which may be any disorder or disease linked to abnormal regulation of protein lysine 3-hydroxybutyrylation or de-lysine-3-hydroxybutyrylation, respectively. Examples of such disorder or disease may include cancer, neurodegenerative diseases, aging, metabolic disorder, and dysgenesis.

The determination method of the present invention may further comprise comparing the FRET level in the sample with a control FRET level. The control FRET level may be the FRET level in a control sample obtained from a subject, who is healthy or has not suffered from or predisposed to a protein lysine 3-hydroxybutyrylation related disorder. The FRET level in the sample may be higher or lower than the control FRET level.

The determination method of the present invention may further comprise adding an agent to the sample. In some embodiments, the agent is known to promote or inhibit protein lysine 3-hydroxybutyrylation. In other embodiments, the agent is a screening candidate for a regulator of protein lysine 3-hydroxybutyrylation. The screening candidate may be a compound or a biological molecule.

For each determination method of the present invention, a kit is provided. The kit comprises a fusion protein of the present invention. The kit may further comprise an instruction directing how to carry out the method.

A kit for isolating a peptide containing a 3-hydroxybutyrylated lysine is also provided. The kit comprises an isolated lysine 3-hydroxybutyrylation specific affinity reagent capable of binding specifically to a peptide comprising a 3-hydroxybutyrylated lysine.

A method for treating or preventing a protein lysine 3-hydroxybutyrylation related disease in a subject in need thereof is provided. The method comprises administering to the subject an effective amount of a composition comprising an agent that regulates protein lysine 3-hydroxybutyrylation. The agent may be a screen candidate identified by a determination method of the present invention. The protein lysine-3-hydroxybutyrylation may be histone lysine-3-hydroxybutyrylation.

A method for treating or preventing a protein or de-lysine-3-hydroxybutyrylation related disease in a subject in need thereof is provided. The method comprises administering to the subject an effective amount of a composition comprising an agent that regulates protein de-lysine-3-hydroxybutyrylation. The agent may be a screen candidate identified by a determination method of the present invention. The protein de-lysine-3-hydroxybutyrylation may be histone de-lysine-3-hydroxybutyrylation.

EXAMPLE 1

Materials and Methods

Peptide Sample Preparation

Synthesis and characterization of modified lysine residues used for peptide synthesis is described in the Additional Methods published online. Trypsin digestion of histones and whole-cell lysate samples was performed as previously described. Ten milligrams of whole-cell lysate tryptic digest was separated into 80 fractions with basic reversed phase HPLC. The peptide fractions were concatenated into 20 fractions and subjected to immunoaffinity enrichment for $K_{3ohbu}$ peptides using a similar method previously described.

MS/MS Data Analysis

Peptide sample was analysed by HPLC-MS/MS and the data was searched against an IPI human (v3.70) or IPI mouse (v3.74) database. Bioinformatic analyses were performed as previously described with a Benjamini-Hochberg false discovery rate of 1%. Detailed methods were described in the Additional Methods published online.

Cell Culture and Animal Experiments

HEK293 cells were grown in complete DMEM medium either not treated, or treated with chemicals at conditions specified elsewhere in the text. C57BL/6 mice were either fed with standard chow diet, or fasted (with free access to water) for a specified number of hours as detailed in the text. C57BKS/J db/db littermates (licensed by the Jackson Laboratory) were either given single-dose intraperitoneal injections of streptozotocin (STZ, 200 mg/kg body weight), or the sodium citrate buffer vehicle for 48 hours. The liver tissues were collected for histone extraction and western blot analysis.

Reagents

The pan anti-$K_{3ohbu}$ antibody was co-developed with PTM Biolabs, Inc. (Chicago, Ill.). Peptides were synthesized using racemic or enantiomeric modifier protected amino acid residues. Synthesis of Fmoc-protected amino acid residues is described in detail in Supplementary Methods. Modified sequencing-grade trypsin was purchased from Promega (Madison, Wis.). C18 ZipTips were bought from Millipore Corporation (Bedford, Mass.). Other chemicals were obtained from the following suppliers. Sigma-Aldrich (St. Louis, Mo.): formic acid (>98%), $NH_4HCO_3$ (>99%), trichloroacetic acid (6.1 N), iodoacetamide, dithiothreitol, bovine serum albumin, sodium butyrate, nicotinamide, trichostatin A, Fmoc-Lys—OH (98%), Sodium (R/S)-3-Hydroxybutyrate-2,4-$^{13}C_2$ (99 atom %), (R/S)-3-hydroxybutyrate, (R)-3-hydroxybutyrate, (S)-3-hydroxybutyrate, 2-hydroxyisobutyric acid (98%), N-hydroxysuccinimide (98%), $H_3PO_4$ (99%), $BF_3.OEt_2$, isobutylene (99%), LiOH (>98%), 4-butyrolactone (>99%), trityl chloride (98%), anhydrous pyridine (99.8%), ethyl (R)-3-hydroxybutyrate (98%), ethyl (S)-3-hydroxybutyrate (99%), N,N'-dicyclohexylcarbodiimide (DCC) (99%), anhydrous dioxane (99.8%), methyl (S)-3-hydroxy-2-methylpropionate (99%), methyl (R)-3-hydroxy-2-methylpropionate (99%), trifluoroacetic acid (99%), and ethyl 2-hydroxybutyrate (>95% GC). Fisher (Pittsburgh, Pa.): $NaHCO_3$ (ACS grade), NaOH (ACS grade), $CH_3CN$ (HPLC grade), $CH_2Cl_2$ (HPLC grade), HCl solution (37.3%), MeOH (ACS grade), acetone (ACS grade), EtOAc (ACS grade), anhydrous $Et_2O$ (ACS grade), DMEM medium (high glucose), anhydrous $Na_2SO_4$ (ACS grade), anhydrous $MgSO_4$ (ACS grade), hexane (ACS grade), $Et_3N$ (>99%), and hydrogen peroxide. Abcam: anti-histone H3 antibody, anti-alpha tubulin antibody.

Cell Culture and Preparation of Peptide Samples

HEK293 cells were grown to 90% confluence in complete DMEM medium at 37° C. in a humidified incubator supplemented with 5% $CO_2$. For isotopic labelling, HEK293 cells were grown in complete DMEM medium containing 20 mM (R/S)-3-hydroxybutyrate [2,4-$^{13}C_2$] for 48 hrs until they reached 95% confluence. For identification of 3-hydroxybutyrylation substrates, HEK293 cells were grown in complete DMEM medium treated with or without sodium 3-hydroxybutyrate as specified elsewhere in the paper. The cells were lysed in lysis buffer (100 mM NaCl, 20 mM Tris, 0.5 mM EDTA, 0.5% (v/v) NP40, 0.2 mM PMSF, 2 µg/µL leupeptin, 10 µg/mL aprotinin, 5 mM sodium butyrate and 10 mM nicotinamide) at 4° C. for 20 min with constant rotation. The sample was centrifuged for 10 min at 4° C. at 20,000× g. The insoluble pellet was resuspended in 10 volumes of lysis buffer followed by brief sonication at 4° C. The protein lysate samples were combined and precipitated in 80% cold acetone (pre-chilled to −20° C.) and 10% trichloroacetic acid solution at −20° C. for 2 hrs. The protein pellet was washed twice with cold acetone and the sample was digested with 50:1 sequencing grade modified trypsin (Promega) at 37° C. for 16 hrs. The digestion was reduced with 5 mM dithiothreitol at 50° C. for 30 min, alkylated with 15 mM iodoacetamide at rt for 30 min, and blocked with 30 mM cysteine at rt for 30 min. After reduction and alkylation, the sample was digested with 100:1 trypsin at 37° C. for an additional 4 hrs. For proteomic identification of $K_{3ohbu}$ substrates from HEK293 cells, the tryptic peptides were further separated by reversed phase chromatography as described below.

Animal Experiments

All animal experiments were approved by the Animal Ethics Committee of the Shanghai Institute of Materia Medica, China, where the experiments were conducted. For the starvation experiment, two groups of 16 weeks old adult C57BL/6 mice (control group: n=20, 10 males and 10 females; experimental group: n=40, 20 males and 20 females) were either fed with standard chow diet containing 19% protein, or fasted (with free access to water) for 24, 48 and 72 hours (9:00 am to 9:00 am) as detailed in the text.

C57BKS/J db/db mice were licensed from the Jackson Laboratory and bred in house. All mice were housed in a temperature-controlled room (22±2° C.), with a light/dark cycle of 12 h/12 h. At the age of 12 weeks, C57BKS/J db/db littermates (C57BLKS/J lean mice) were recruited to the experiment and randomly assigned. For the ketoacidosis experiment, db-littermate mice (n=6 for each group, 3 males and 3 females) were either given single-dose intraperitoneal injections of streptozotocin (STZ, 200 mg/kg body weight), or the sodium citrate buffer vehicle. After 48 hrs (9:00 am to 9:00 am), blood samples were taken from a tail vein for determination of blood glucose and 3-hydroxybutyrate concentrations using a gluco-ketone meter (Lifescan, Burnaby, BC, Canada). The mice were decapitated and liver tissue was collected for histone extraction and lysate preparation.

Extraction of Histones

Extraction of core histones from HEK293 cells and mouse liver was carried out according to a previously described protocol with minor modifications. Liver samples were homogenized using a glass Dounce homogenizer (20 strokes) in ice-cold lysis buffer. The homogenate was passed through two layers of cheese cloth and then centrifuged at 1,000× g at 4° C. for 5 min. The pellet was briefly washed with lysis buffer and extracted with 0.4 N $H_2SO_4$ at 4° C. overnight. HEK293 cells were lysed in lysis buffer on ice for 10 min with gentle stirring. The lysate was removed and the pellet was washed once with the lysis buffer and then extracted with 0.4 N $H_2SO_4$ at 4° C. overnight. The suspension was centrifuged at 20,000× g for 10 min at 4° C. The histone-containing supernatants were precipitated with 20% trichloroacetic acid. The precipitated histone pellets were washed twice with cold acetone and dried. The histone samples were then digested with sequencing grade trypsin as described earlier.

Reversed Phase Fractionation of Tryptic Peptides

Peptide fractionation by reversed-phase chromatography was performed on a Phenomenex Luna C18 column (10 mm×250 mm, 5 μm particle, 100 Å pore size) with a flow rate of 4 mL/min using the Shimadzu preparative HPLC system. Buffer A consisted of 10 mM ammonium formate in water (pH 7.8) and buffer B consisted of 10 mM ammonium formate in 90% acetonitrile (pH 7.8). Peptides were loaded onto the column in 2 mL of buffer A and eluted with a gradient of 2-30% B in 40 min and 30-90% B in 10 min. A total of 80 fractions were collected and concatenated into 20 fractions. Acetonitrile was removed from each fraction using a Rotavapor evaporator connected to a water pump; the remaining samples were dried by lyophilisation. Immunoaffinity enrichment of $K_{3ohbu}$ peptides was performed as previously described.

HPLC-Mass Spectrometry Analysis

Tryptic peptides were dissolved in HPLC buffer A (0.1% formic acid in water) and loaded onto a self-packed C18 capillary column (10 cm in length, 75 μm ID) packed with Jupiter C12 resin (Phenomenex, 90 Å, 4 μm in size) by Eksigent 1D-plus nano-flow HPLC. Peptides were eluted with a linear gradient of 5%-30% B in 2 hrs with a constant flow rate of 200 nL/min. Peptide ions were directly electrosprayed into a LTQ Velos Orbitrap mass spectrometer and analysed by either fragmenting the 20 most intense ions in a data-dependant mode, or fragmenting specified precursor ions for targeted analysis by collision-induced dissociation.

Peptide Identifications and Quantifications

MS/MS data were analyzed by Maxquant (v1.3.0.5) with a built-in Andromeda search engine against an IPI human (v3.70) or IPI mouse (v3.74) database for protein and peptide identification. Lys acetylation, 3-hydroxybutyrylation, methionine oxidation, and protein N-terminal acetylation were specified as variable modifications. Mass tolerance was set to 6 ppm for precursor ions and 0.5 Da for fragment ions. Results were filtered at a 1% false discovery rate at protein, peptide and site levels. To reduce the number of low quality PTM identifications, we further remove all peptides with Maxquant peptide score below 60 or site localization probability below 0.9. We also removed all peptide identification with C-terminal Lys modifications and peptide identifications from known contaminant proteins.

Bioinformatic Analysis

Statistical gene enrichment and under-enrichment analysis for Gene Ontology (GO), Kyoto Encyclopedia of Genes and Genomes (KEGG) pathway and Pfam domains was performed as previously described with a Benjamini-Hochberg false discovery rate of 1%. The manually curated CORUM protein complex database for mouse and human was used for protein complex analysis. Overrepresented complexes were identified using the hypergeometric test with a Benjamini-Hochberg false discovery rate of 1%, and were visualized in Cytoscape. Protein-protein interactions involving Lys-3-hydroxybutyrylated proteins were extracted from the STRING database and interaction sub-networks were identified by the MCODE plug-in tool in Cytoscape. Flanking sequence preference was analyzed by Icelogo with $p<0.05$. Sequence motif identification was performed by motif-x (Bonferroni $p<0.05$) and visualized by Weblogo.

Synthesis and Characterization of Modified Lysine Residues Used for Peptide Synthesis Fmoc-Lys(2-hydroxyisobutyryl)—OH. DCC (32.6 mM, 6.72 g) was added to a solution of 2-hydroxyisobutyric acid (32 mM, 3.35 g) and N-hydroxysuccinimide (32.6 mM, 3.75 mg) in 30 mL anhydrous $CH_3CN$. The resulting mixture was stirred at rt for 3 hrs and then filtered. The filtration was evaporated to dryness. The residue was redissolved in 300 mL $CH_2Cl_2$, and $Et_3N$ (64 mM, 8.9 mL) and Fmoc-Lys—OH (32 mM, 12.9 g) were added. The mixture was stirred at rt for 8 hrs. The solvent was evaporated and the residue was redissolved in water. The pH of the solution was adjusted to 2.0. The aqueous solution was extracted 3 times with ethyl acetate. The organic phases were combined, washed with brine and dried over anhydrous $Na_2SO_4$. The solvent was reduced to dryness and the residue was purified through flash column chromatography (eluent: $MeOH/CH_2Cl_2=1/40$ to 1/20). A yield of 8.7 g (60%) Fmoc-Lys(2-hydroxyisobutyryl)—OH was obtained. Fmoc-Lys(2-hydroxyisobutyryl)—OH: $^1$H NMR (500 MHz, $CDCl_3$): δ 7.69 (d, J=7.5

Hz, 2H), 7.54 (t, J=7.5 Hz, 2H), 7.33 (t, J=7.5 Hz, 2H), 7.23 (t, J=7.5 Hz, 2H), 5.99 (d, J=8.0 Hz, 1H), 4.30-4.40 (m, 3H), 4.12-4.14 (m, 1H), 3.18-3.19 (m, 2H), 1.64-1.84 (m, 2H), 1.37-1.47 (m, 10H); $^{13}$C NMR (125 MHz, CDCl$_3$): δ 177.6, 174.9, 156.4, 143.7 (143.6), 141.2 (141.1), 127.7, 127.0, 125.0, 119.9, 73.5, 67.1, 53.6, 47.0, 38.6, 31.6, 28.7, 27.5 (27.4), 22.1; IR (KBr): 3361.7, 2934.8, 2868.3, 1711.2, 1696.9, 1642.5, 1631.6, 1536.4, 1454.6, 1270.5, 1254.9, 1200.1, 1176.6, 1047.3, 765.4, 740.3 cm$^{-1}$; HRMS (m/z): [M]$^+$ calcd. for C$_{25}$H$_{31}$N$_2$O$_6$, 455.2182; found, 455.2165.

Fmoc-Lys((±)-2-($^t$BuO) butyryl)—OH. Step 1: Racemic ethyl 2-hydroxybutyrate (15.1 mM, 1.78 g, 1.83 mL) was dissolved in 25 mL CH$_2$Cl$_2$. Then, 2 g of 99% H$_3$PO$_4$ and 312 µL BF$_3$.OEt$_2$ was added in sequential order. The resulting mixture was cooled in an ice-acetone bath and stirred. Then, 10 mL isobutylene measured in a 50 mL cylinder (pre-cooled in a dry ice acetone bath) was poured into the flask. The flask was sealed and the reaction was stirred under −78° C. for 1 hr, then allowed to return to rt. After 10 hrs, the isobutylene was discharged and the solvent was evaporated to dryness. The residue was redissolved in 100 mL EtOAc. The solution was washed 3 times with saturated NaHCO$_3$ solution, followed by brine. The organic layer was separated and dried over anhydrous Na$_2$SO$_4$. The solvent was evaporated and the residue was purified through flash column chromatography. The column was first eluted with 50 mL hexane/triethylamine (v/v=50/1), then with 200 mL hexane/CH$_2$Cl$_2$ (v/v=7/1), followed by 200 mL hexane/EtOAc (v/v=8/1). A yield of 1.31 g (50%) ethyl 2-($^t$BuO) butyrate was obtained.

Step 2: Ethyl 2-($^t$BuO) butyrate (1.31 g, 7 mM) was dissolved in 20 mL MeOH/H$_2$O=1/1 solution. Then, LiOH (25 mM, 575 mg) was added. The mixture was stirred at rt for 1.5 hrs. Fifty milliliters of water was added. The solution was washed with Et$_2$O (30 mL×2) to remove some impurities. Then, the aqueous layer was separated and acidified with 1 M HCl solution to pH 2.3. The aqueous solution was extracted 3 times with EtOAc. The organic layer was combined, washed with brine and dried over anhydrous Na$_2$SO$_4$. The solvent was filtered and evaporated to give the crude product 2-($^t$BuO) butyric acid which was used in the next step without further purification.

Step 3: DCC (6.5 mM, 1.31 g) was added to a solution (80 mL) of 2-($^t$BuO) butyric acid (1.04 g, 6.5 mM) and N-hydroxysuccinimide_ (6.5 mM, 748 mg) in CH$_3$CN. The reaction was stirred at rt for 4 hrs. The resulting suspension was filtered and concentrated under vacuum. The residue was redissolved in 100 mL CH$_2$Cl$_2$. Et$_3$N (13 mM, 1.81 mL) and Fmoc-Lys—OH (6.5 mM, 2.62 g) were sequentially added. The reaction mixture was stirred at rt for 8 hrs and then evaporated, and the residue was dissolved in 150 mL water. The solution was adjusted to pH 2.3. The organic layer was separated and the aqueous layer was extracted 3 times with EtOAc. The combined organic layers were dried over anhydrous Na$_2$SO$_4$. The residue was purified through flash column chromatography (eluent: MeOH/CH$_2$Cl$_2$=1/40 to 1/20). A yield of 2.5 g (75%) Fmoc-Lys(2-($^t$BuO) butyryl)—OH was obtained. $^1$H NMR (500 MHz, CDCl$_3$): δ 9.73 (s, 1H), 7.73 (d, J=7.5 Hz, 2H), 7.54-7.61 (m, 2H), 7.36 (t, J=7.5 Hz, 2H), 7.28 (t, J=7.5 Hz, 2H), 6.87-6.90 (m, 1H), 5.85 (dd, J=27.5, 9.0 Hz, 1H), 4.28-4.44 (m, 3H), 4.15-4.19 (m, 1H), 3.91-3.94 (m, 1H), 3.19-3.36 (m, 2H), 1.38-1.92 (m, 8H), 1.17 (1.15) (s, 9H), 0.88 (q, J=7.0 Hz, 3H); $^{13}$C NMR (125 MHz, CDCl$_3$): δ 175.7, 174.6, 156.1, 143.87 (143.86, 143.70, 143.68), 141.2, 127.6, 127.0, 125.2 (125.1), 119.8, 75.3 (75.2), 73.6 (73.5), 67.0, 53.6, 47.1, 38.4 (38.4), 31.84 (31.2), 29.22 (29.16), 27.89 (27.87), 27.67 (27.66), 22.22 (22.18), 9.42 (9.36); IR (KBr): 3404, 3336, 3065, 2973, 2936, 2875, 1718, 1632, 1538, 1451, 1338, 1255, 1192, 1107, 1081, 1057, 1005, 760, 740 cm$^{-1}$; HRMS (m/z): [M]$^+$ calcd. for C$_{29}$H$_{39}$N$_2$O$_6$, 511.2808; found, 511.2787.

Fmoc-Lys((S)-3-($^t$BuO)isobutyryl)—OH, Fmoc-Lys((R)-3-($^t$BuO)isobutyryl)—OH, Fmoc-Lys((R)-3-($^t$BuO)butyryl)—OH and Fmoc-Lys((S)-3-($^t$BuO)butyryl)—OH were synthesized in a similar manner to Fmoc-Lys((±)-2-($^t$BuO) butyryl)—OH, starting from different raw materials. Fmoc-Lys((±)-3-($^t$BuO)isobutyryl)—OH: $^1$H NMR (500 MHz, CDCl$_3$): δ 9.76 (s, 1H), 7.72 (d, J=7.5 Hz, 2H), 7.58 (dd, J=10.0, 8.0 Hz, 2H), 7.35 (t, J=7.5 Hz, 2H), 7.26 (t, J=7.5 Hz, 2H), 6.85 (t, J=6.0 Hz, 1H), 5.91 (t, J=8.0 Hz, 1H), 4.29-4.41 (m, 3H), 4.16-4.18 (m, 1H), 3.38-3.39 (m, 2H), 3.18-3.30 (m, 2H), 2.42-2.48 (m, 1H), 1.47-1.94 (m, 2H), 1.41-1.53 (m, 4H), 1.14 (s, 9H), 1.11 (d, J=7.5 Hz, 3H); $^{13}$C NMR (125 MHz, CDCl$_3$): δ 176.2 (176.1), 174.6, 156.2, 143.8 (143.7), 141.1, 127.5, 126.9, 125.09 (125.05), 119.8, 73.6, 66.9, 63.8 (63.7), 53.6, 47.0, 40.99 (40.97), 38.8, 31.7, 29.0, 27.265 (27.260), 22.2, 14p.0 (13.9); IR (KBr): 3334, 3066, 2974, 2927, 2872, 1726, 1657, 1541, 1450, 1364, 1335, 1235, 1028, 876, 760, 739 cm$^{-1}$; HRMS (m/z): [M]$^+$ calcd. for C$_{29}$H$_{39}$N$_2$O$_6$, 511.2808; found, 511.2791.

Fmoc-Lys((S)-3-($^t$BuO) butyryl)—OH: $^1$H NMR (500 MHz, CDCl$_3$): δ 9.23 (s, 1H), 7.73 (d, J=7.5 Hz, 2H), 7.58 (t, J=7.5 Hz, 2H), 7.36 (t, J=7.5 Hz, 2H), 7.27 (t, J=7.5 Hz, 2H), 6.87-6.89 (m, 1H), 5.85 (d, J=8.0 Hz, 1H), 4.33-4.46 (m, 3H), 4.16-4.19 (m, 1H), 4.01-4.07 (m, 1H), 3.31-3.38 (m, 1H), 3.12-3.18 (m, 1H), 2.61 (ddd, J=52.5, 14.5, 6.5 Hz, 2H), 1.78-1.95 (m, 2H), 1.38-1.57 (m, 4H), 1.15-1.16 (m, 12H); $^{13}$C NMR (125 MHz, CDCl$_3$): δ 174.6, 172.4, 156.1, 143.9 (143.7), 141.2, 127.6, 126.99 (126.97), 125.12 (125.09), 119.9, 74.7, 66.9, 65.1, 53.6, 47.1, 45.2, 38.9, 31.9, 28.9, 28.2, 22.8, 22.3; IR (KBr): 3332, 3065, 2974, 2935, 2869, 1718, 1653, 1541, 1450, 1366, 1208, 1106, 1084, 1053, 989, 760, 740 cm$^{-1}$; HRMS (m/z): [M]$^+$ calcd. for C$_{29}$H$_{39}$N$_2$O$_6$, 511.2808; found, 511.2787.

Fmoc-Lys(4-(tritylO)butyryl)—OH. Step 1: A mixture of 2.58 g (30 mM, 2.28 mL) of 4-butyrolactone and 1.2 g (30 mM) of sodium hydroxide in 30 mL of water was heated at 70° C. overnight. The clear solution was cooled and concentrated. The resulting white solid was suspended in toluene and concentrated further to remove the remaining trace amounts of water. An almost quantitative yield of sodium 4-hydroxybutyrate was obtained.

Step 2: Sodium 4-hydroxybutyrate (1.26 g, 10 mM) and trityl chloride (10 mM, 2.79 g) were dissolved in 30 mL pyridine for 3 days at 30° C. The solvent was evaporated and the residue was dissolved in ethyl ether. The ether solution was extracted with aqueous sodium hydroxide solution (4 g in 250 mL of H$_2$O). The aqueous solution was acidified to pH 3.0 and extracted twice with ethyl acetate. The combined organic phases were washed with brine and dried over anhydrous MgSO$_4$. The mixture was filtered and the filtration was evaporated to dryness give the solid product 4-(tritylO) butyric acid (1.29 g, 37%).

Step 3: DCC (3.7 mM, 760 mg) was added to a solution of 4-(tritylO) butyric acid (1.29 g, 3.7 mmol) and N-hydroxysuccinimide (3.7 mM, 425 mg) in 30 mL dioxane. The reaction was stirred at rt for 10 hrs. The solution was filtered and evaporated to dryness, and then the residue redissolved in 60 mL CH$_2$Cl$_2$. Et$_3$N (8 mM, 1.2 mL) and Fmoc-Lys—OH (4 mM, 1.62 g) were sequentially added. The mixture was stirred at rt for 4 hrs. After that, 150 mL water was added to the mixture and the solution was adjusted to pH 2.3. The organic layer was separated and the aqueous layer was extracted with EtOAc. The combined organic layers were dried over anhydrous $Na_2SO_4$. The solvent was evaporated and the residue was purified by flash column chromatography (MeOH/$CH_2Cl_2$=1/30). A yield of 1.5 g crude Fmoc-Lys(4-(tritylO) butyryl)—OH was obtained. The crude product contains more than 20% 1,3-dicyclohexylurea (DCU) based on the MS result, but it is pure enough for peptide synthesis. Fmoc-Lys(4-tritylO butyryl)—OH: $^1$H NMR (500 MHz, $CDCl_3$): δ 8.03 (s, 1H), 7.69-7.72 (m, 2H), 7.49-7.57 (m, 2H), 7.31-7.42 (m, 7H), 7.23-7.29 (m, 12H), 5.88 (t, J=5.5 Hz, 1H), 5.83 (d, J=8.5 Hz, 1H), 4.28-4.44 (m, 3H), 4.09-4.20 (m, 1H), 3.04-3.17 (m, 4H), 2.28 (t, J=7.5 Hz, 2H), 1.67-1.94 (m, 4H), 1.26-1.39 (m, 4H); $^{13}$C NMR (125 MHz, $CDCl_3$): δ 174.8, 174.0, 156.2, 144.1 (144.0), 143.9 (143.7), 141.2, 128.6 (128.5), 127.8 (127.7), 127.6, 127.03 (127.01), 127.98 (127.93), 125.15 (125.09), 119.9, 86.6, 67.0, 62.5, 53.6, 47.1, 39.0, 33.7, 31.7, 28.9, 26.0, 22.1; IR (KBr): 3420, 3325, 3059, 2934, 2869, 1718, 1653, 1539, 1492, 1449, 1419, 1336, 1265, 1221, 1073, 760, 740, 707 $cm^{-1}$; HRMS (m/z): $[M]^+$ calcd. for $C_{44}H_{45}N_2O_6$, 697.3278; found, 697.3268.

Results and Discussion

To search for possible novel histone marks, we analyzed a tryptic digest of core histones from HEK293 cells by HPLC/MS/MS. The generated MS/MS data were subjected to non-restrictive sequence alignment, searching for amino acid residues bearing mass shifts that were different from those of known PTMs. The analysis detected a previously undescribed mass shift of +86.0368 Da±0.02 Da (monoisotopic mass) at lysine residues of multiple histone peptides. This mass shift is therefore possibly caused by a new PTM. We used the accurately determined mass shift to predict the elemental composition of the modification, the most likely elemental composition for the modification moiety was $C_4H_7O_2$ (formula of mass shift plus one proton). This molecular formula has seven possible structural isomers: R- and S-isoforms of 3-hydroxybutyryl (3ohbu) (two possible enantiomers, the R- and S-isoforms, for the 3-hydroxybutyryl group), 3-hydroxyisobutyryl (3ohibu), R- and S-2-hydroxybutyryl (2ohbu), 2-hydroxyisobutyryl (2ohibu), and 4-hydroxybutyryl (4ohbu) (FIG. 1a).

We used chemical methods to determine the structural isomers responsible for the detected mass shift. We first synthesized variants of two substrate histone peptides, $K_{+86.0276}QLATK_{ac}AAR$ (SEQ ID NO: 29) and $PEPAK_{+86.0374}SAPAPK$ (SEQ ID NO: 113), incorporating each of the seven possible isomers at the sites of the mass shift. As expected, the synthetic $K_{3ohbu}$-containing H2BK5 peptides with the sequence $PEPAK_{3ohbu}SAPAPK$ (SEQ ID NO: 113), either with a R-isoform, $K_{(R)-3ohbu}$, or S-isoform, $K_{(S)-3ohbu}$, co-eluted in HPLC/MS analysis, because enantiomers are impossible to be separated in a reverse-phase HPLC non-chiral column. Likewise, a mixture of $K_{(R)-3ohbu}QLATK_{ac}AAR$ (SEQ ID NO: 29) and $K_{(S)-3ohbu}QLATK_{ac}AAR$ (SEQ ID NO: 29) co-eluted, which was used for subsequent co-elution experiment. Because R-3-hydroxybutyryl-CoA is an important metabolite for lipid metabolism and R-3-hydroxybutyrate is a major component of ketone bodies, we chose lysine R-3-hydroxybutyrylation as the more likely candidate. In the rest of this paper, all the 3-hydroxybutyrylation and lysine 3-hydroxybutyrylation are referred as R-isoform instead of S-isoform unless specified.

The synthetic peptide, $K_{3ohbu}QLATK_{ac}AAR$ (SEQ ID NO: 29), co-eluted with the corresponding in vivo-derived peptide, $K_{+86.0276}QLATK_{ac}AAR$ (SEQ ID NO: 29), on HPLC, and had the same fragmentation pattern in HPLC/MS/MS (FIG. 2a, b, and d). In contrast, the in vivo-derived peptide $K_{+86.0276}QLATK_{ac}AAR$ (SEQ ID NO: 29) had a different HPLC retention time than the other four synthetic structural isomers with identical mass, $K_{3ohibu}QLATK_{ac}AAR$ (SEQ ID NO: 29), $K_{2ohbu}QLATK_{ac}AAR$ (SEQ ID NO: 29) (R/S mixture), $K_{2ohibu}QLATK_{ac}AAR$ (SEQ ID NO: 29) and $K_{4ohbu}QLATK_{ac}AAR$ (SEQ ID NO: 29). Using the same method, we confirmed that the mass shift in the peptide $PEPAK_{+86.0374}SAPAPK$ (SEQ ID NO: 113) is also caused by lysine R-3-hydroxybutyrylation. Together, these data lead us to conclude that the identified mass shift of +86 Da is caused by lysine 3-hydroxybutyrylation, but not other structural isomers.

Next, we generated a pan antibody against R-3-hydroxybutyrylation (anti-$K_{3ohbu}$) using methods previously described, and used the antibody to further confirm lysine R-3-hydroxybutyrylation. The antibody showed good specificity in dot blot assay and competition experiments. In immunostained HEK293 cells, the PTM was mostly detected in nuclei. Treating the cells with sodium R-3-hydroxybutyrate at 10 mM, a concentration comparable to the range of 3-hydroxybutyrate concentrations in human diabetic ketoacidosis, dramatically enhanced nuclear lysine 3-hydroxybutyrylation. R-3-hydroxybutyrate and (R/S)-3-hydroxybutyrate (20 mM), but not S-3-hydroxybutyrate (20 mM), drastically induced Lys 3-hydroxybutyrylation in HEK293 cells, indicating that R-3-hydroxybutyrate is likely the main substrate leading to R-3-hydroxybutyrylation. Western blot analysis of whole cell lysate samples showed that $K_{3ohbu}$ is present in Escherichia coli (strain ME9062), Drosophila melanogaster S2 cells, mouse embryonic fibroblast (MEF) cells and HEK293 cells (FIG. 3a).

Because short-chain-CoAs are cofactors for a variety of lysine acylations, R-3-hydroxybutyryl-CoA may also be the cofactor for the lysine 3-hydroxybutyrylation reaction. R-3-hydroxybutyryl-CoA can be synthesized by several metabolic pathways (FIG. 1b). Alternatively, it may be generated from cellular 3-hydroxybutyrate, possibly by 3-hydroxyacyl-Coenzyme A synthetase, in the same way that acetate and crotonate can be converted to their corresponding CoA derivatives. To test this hypothesis, we first treated HEK293 cells with 10 mM R-3-hydroxybutyrate and then examined lysine modifications by Western blot. We observed a dramatic increase in global Lys $K_{3ohbu}$ in the treated cells compared to the control. Cells treated with crotonate also showed a slight increase in Lys $K_{3ohbu}$, possibly caused by a slight increase in 3-hydroxybutyryl-CoA due to interconversion between crotonyl-CoA and 3-hydroxybutyryl-CoA. These results not only validate $K_{3ohbu}$ but also imply that 3-hydroxybutyryl-CoA is the cofactor used for $K_{3ohbu}$, just as acetyl-CoA and crotonyl-CoA are used for protein lysine acetylation and lysine crotonylation, respectively.

To confirm this possibility, we treated HEK293 cells with 20 mM isotopically labelled (R/S)-3-hydroxybutyrate [2,4-$^{13}C_2$], followed by HPLC/MS/MS analysis of histone peptides from the cells using a procedure similar to the one previously described. We found the isotopically labelled $K_{3ohbu}$ peptides have an additional mass shift of 2 Da (e.g., 88.0328 Da vs 86.0276 Da in FIG. 2c). In addition, these peptides have the same fragmentation patterns as the corresponding in vivo-derived and synthetic $K_{3ohbu}$-containing peptides (FIG. 2a-c). Together, we identified 30 $K_{3ohbu}$-containing histone peptides bearing isotopically labelled $K_{3ohbu}$ as validated by an additional mass shift of 2 Da.

3-hydroxybutyrate constitutes a major component of ketone bodies (FIG. 1b) and its concentration can dramatically increase by more than 10-fold during starvation and over 20-fold in pathological conditions such as Type 1 diabetes (T1DM) and alcoholic liver damage (up to 20 mM). Thus, $K_{3ohbu}$ levels may also change in response to an increased 3-hydroxybutyrate that may in turn enhance the concentration of 3-hydroxybutyrate CoA. To test this possibility, we examined $K_{3ohbu}$ abundance by Western blot analysis using the liver samples from C57BL6 mice either fed with a normal chow or fasted (supplied with water only). Our results showed that $K_{3ohbu}$ was drastically up-regulated after 48 hours of fasting (FIG. 3b) relative to the control. The increase of $K_{3ohbu}$ is congruent with the observed 7 fold increase in blood 3-hydroxybutyrate concentration in the fasted mice (to an average of about 3.5 mM, n=30) relative to the concentration in the non-fasted controls (which averaged about 0.5 mM, n=20) (FIG. 3d). Consistent with this result, a similar increase in $K_{3ohbu}$ status was observed in mice starved for 24 and 72 hours.

We further examined $K_{3ohbu}$ in the streptozotocin (STZ)-induced type I diabetic mouse model. We observed a much more drastic increase of $K_{3ohbu}$ in liver proteins (FIG. 3c) in the STZ-treated mice compared to the control mice. We found that concentrations of blood glucose and 3-hydroxybutyrate in diabetic littermate mice increased by 2.4- and 10-fold, respectively, 48 hours after the mice were injected with STZ (200 mg/kg body weight; FIG. 3e). Thus, in both fasted and STZ-treated mice, we observed a concerted increase of both 3-hydroxybutyrate concentrations and $K_{3ohbu}$ levels.

Figure 4:
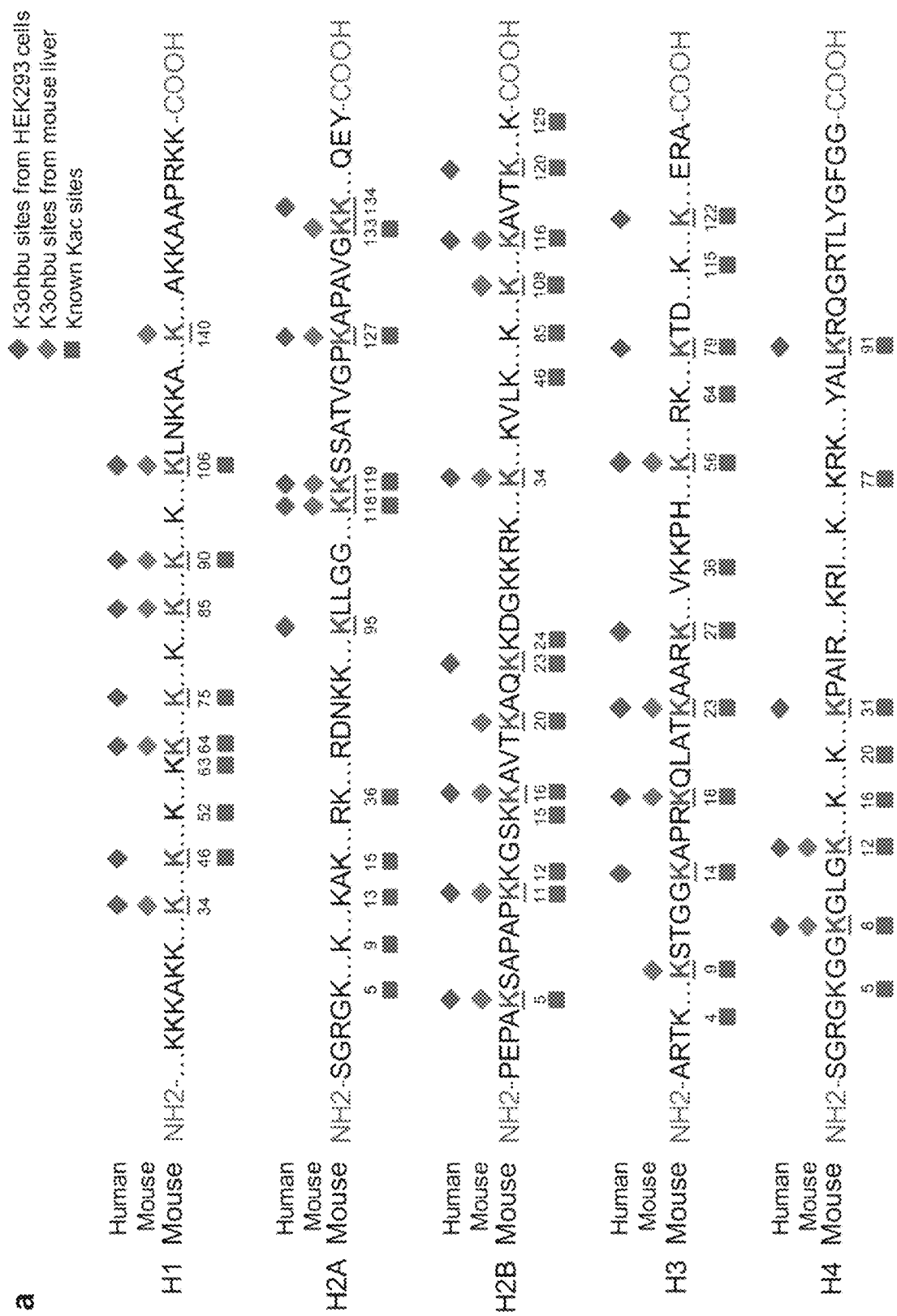
FIG. 4 shows proteomic screening of K$_{3ohbu}$ substrates. (a) K$_{3ohbu}$ sites identified on histones from HEK293 cells (red diamonds) and mouse livers (green diamonds) were mapped to the selected mouse histone sequences for H1 (SEQ ID NO: 108), H2A (SEQ ID NO: 109), H2B (SEQ ID NO: 110), H3 (SEQ ID NO: 111) and H4 (SEQ ID NO: 112) derived from the sequences having UniProtKB accession numbers P15864, P22752, Q6ZWY9, P68433 and P62806, respectively. The modified Lys residues are highlighted in red, and sites known to be lysine-acetylated in human and mouse proteins are marked with blue squares. Cellular compartment analysis of the K$_{3ohbu}$ proteome, showing the enrichment (b) and subcellular distribution (c) of the K$_{3ohbu}$ substrates. (d) Analysis of the sequences surrounding 3-hydroxybutyryllysine in the K$_{3ohbu}$ substrates from the HEK293 dataset identified SK, KxxP, KxA and KxG motifs (Bonferroni-corrected p<0.05). The sequences are shown in Table 3.

Histone marks contribute to epigenetic mechanisms, playing a key role in diverse pathophysiological processes. To map major histone marks bearing $K_{3ohbu}$, we analysed tryptic peptides of core histones from HEK293 cells treated with 10 mM R-3-hydroxybutyrate, and from liver cells of mice that were either fasted for 48 hours or treated with STZ. Together, we identified 45 histone $K_{3ohbu}$ sites, including 38 histone $K_{3ohbu}$ sites from 3-hydroxybutyrate-treated HEK293 cells (FIG. 4a), 21 histone $K_{3ohbu}$ sites from starved mouse liver (FIGS. 4a), and 16 histone $K_{3ohbu}$ sites from STZ-treated diabetic mouse liver (FIG. 4a). Among the 27 $K_{3ohbu}$ sites identified in mouse liver cells, 11 of which were identified in both the STZ-treated diabetic mouse and starved mouse livers.

Identification of $K_{3ohbu}$ substrates on a broad, cellular scale will reveal the scope of the modification and the pathways regulated by it. Additionally, development of a dataset of substrates will lay a foundation for studying non-chromatin functions of $K_{3ohbu}$, as the history of the study of lysine acetylation demonstrates. To this end, we carried out a systematic analysis to identify non-histone substrates bearing $K_{3ohbu}$ in HEK293 cells. Ten milligrams of whole-cell lysate was digested by trypsin and separated into 20 fractions with basic reversed phase HPLC. $K_{3ohbu}$ peptides were affinity-enriched from each fraction using an anti-$K_{3ohbu}$ antibody and then analysed by HPLC-MS/MS. We identified 3232 non-redundant $K_{3ohbu}$ sites in HEK293 cells, with a false discovery rate of less than 1%. We then applied stringent cutoff criteria to further improve the quality of our identification. We removed all site identifications with a Maxquant peptide score below 60 and site localization probability below 0.9. The final dataset identified 3008 non-redundant $K_{3ohbu}$ sites (3156 gene-based $K_{3ohbu}$ sites) from 1359 proteins. The average mass error among these peptides was 0.069 ppm, with a standard deviation of 0.70 ppm.

Functional annotation analysis with gene ontology showed that the $K_{3ohbu}$ proteome is significantly enriched in the nucleus (7.2E-192), intracellular lumen (2.5E-174), cytosolic ribosome (1.8E-22) and mitochondrial matrix (2.4E-12) (FIGS. 4b and c). $K_{3ohbu}$ is abundant in proteins involved in diverse processes related to transcription and metabolism, such as nucleic acid metabolism (1E-130), gene expression (1.0E-97), macromolecular complex organization (5.0E-41), chromatin modification (1.2E-40) and DNA repair (1.6E-31) (table 6b). KEGG pathway enrichment analysis showed that the $K_{3ohbu}$ proteome in HEK293 cells is significantly enriched in 16 complexes or pathways, including spliceosomes (7.2E-43), ribosomes (2.5E-19), RNA transport (2.0E-11), nucleotide excision repair (1.3E-8) and fatty acid elongation in mitochondria (2.3E-3). The spliceosome and ribosome stand out as heavily Lys 3-hydroxybutyrylated complexes when a protein-protein interaction map is constructed among $K_{3ohbu}$ proteins. Analysis of the sequences surrounding $K_{3ohbu}$ sites shows preferences for serine and proline at the −1 and +3 positions, respectively, and alanine and glycine at the +2 position (FIG. 4d). This pattern is different from that seen for Lys acetylation.

To identify macromolecular complexes containing multiple $K_{3ohbu}$ sites, we analysed complex enrichment using the CORUM database and identified over 70 complexes in which a significant proportion of subunits bear $K_{3ohbu}$. Most of these complexes are in the transcription and RNA processing pathways, including the spliceosome (3.5E-124), the ribosome (7.0E-59), the anti-HDAC2 complex (1.64E-27), the ALL-1 supercomplex (1.9E-24), the large Drosha complex (3.6E-23), the LSD1 complex (2.8E-17) and the MeCP1 complex (1.3E-17).

3-Hydroxybutyrate is generated mainly from oxidation of fatty acids in liver under physiological conditions such as starvation and during neonatal development when glucose is not sufficient[1]. Ketosis can also happen when the insulin signaling pathway is not well regulated, as in Type 1 diabetes. During starvation, ketone bodies are important for generating acetyl-CoA as an alternative energy source for the brain and other tissues (e.g., heart and skeletal muscle). Given the dynamic nature of 3-hydroxybutyrate and of $K_{3ohbu}$ levels, $K_{3ohbu}$ may serve as a mechanism for cells to adapt to changes in cellular energy sources (e.g., glucose versus lipids) by rewriting epigenetic programs and modulating the functions of cellular proteins. Emerging evidence suggests that some KDACs have very weak deacetylation activities or activities other than deacetylation. It would be interesting to determine whether any of the KDACs can catalyse removal of 3-hydroxybutyrylation, therefore modulating cellular metabolism.

Several lines of evidence suggest that 3-hydroxybutyrate has functions other than simply providing energy. 3-Hydroxybutyrate has been used successfully to treat epilepsy. It also shows potential for treating several neurological conditions, such as Alzheimer's disease, Parkinson's disease, traumatic brain injury, ischemia, and amyotrophic lateral sclerosis. At the cellular level, R-3-hydroxybutyrate was found to modulate sperm motility, receptor signaling pathways, and autophagy, and to regulate global gene expression profiles associated with cancer cell "stemness". Nevertheless, the molecular mechanisms by which R-3-hydroxybutyrate exerts these functions remain unclear. Discovery of the lysine 3-hydroxybutyrylation pathway therefore illuminates a new direction in studying the diverse physiological functions of R-3-hydroxybutyrate and its pharmacological significance.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

TABLE 1

List of histone K3ohbu sites identified from HEK293 cells treated with 10 mM sodium R-3-hydroxybutyrate for 72 hours. "K(3ohbu)" and "K(ac)" indicates 3-hydroxybutyrylated lysine and acetylated lysine, respectively.

| Human histone protein | Position | Peptide Sequence | SEQ ID NO |
|---|---|---|---|
| H1 | 149 | K(3ohbu)LAATPK | 30 |
| H1 | 23 | VTK(3ohbu)AGGSAALSPSK | 31 |
| H1 | 34 | AGGSAALSPSK(3ohbu)K | 32 |
| H1 | 143 | GAPAAATAPAPTAHK(3ohbu)AK | 33 |
| H1 | 207 | PSVPK(3ohbu)VPK | 34 |
| H1 | 85 | LGLK(3ohbu)SLVSK | 35 |
| H1 | 90 | SLVSK(3ohbu)GTLVQTK | 36 |
| H1 | 106 | GTGASGSFK(3ohbu)LNK | 37 |
| H1 | 34 | K(3ohbu)ASGPPVSELITK | 38 |
| H1 | 46 | ASGPPVSELITK(3ohbu)AVAASK | 39 |
| H1 | 64 | K(3ohbu)ALAAAGYDVEK | 40 |
| H1 | 97 | GTLVQTK(3ohbu)GTGASGSFK | 41 |
| H1 | 75 | ALAAAGYDVEK(3ohbu)NNSR | 42 |
| H1 | 168 | K(3ohbu)PAAATVTK | 43 |
| H2A | 5 | AGGK(3ohbu)AGK(ac)DSGK | 44 |
| H2A | 12 | AGK(ac)DSGK(3ohbu)AK | 45 |
| H2A | 120 | K(3ohbu)TSATVGPK | 46 |
| H2A | 128 | TSATVGPK(3ohbu)APSGGK(ac)K | 47 |
| H2A | 135 | K(3ohbu)ATQASQEY | 48 |
| H2A | 123 | GK(3ohbu)LEAIITPPPAK | 49 |
| H2A | 37 | K(3ohbu)GNYAER | 50 |
| H2A | 96 | NDEELNK(3ohbu)LLGK | 51 |
| H2A | 119 | VTIAQGGVLPNIQAVLLPK(3ohbu)K | 52 |
| H2B | 6 | PEPTK(3ohbu)SAPAPK | 53 |
| H2B | 12 | SAPAPK(3ohbu)K(ac)GSK | 54 |
| H2B | 17 | GSK(ac)K(3ohbu)AVTK | 55 |
| H2B | 21 | AVTK(3ohbu)AQK | 56 |
| H2B | 35 | K(3ohbu)ESYSVYVYK | 57 |
| H2B | 117 | HAVSEGTK(3ohbu)AVTK | 58 |
| H2B | 121 | AVTK(3ohbu)YTSSK | 59 |
| H2B | 6 | PELAK(3ohbu)SAPAPK | 60 |
| H2B | 17 | K(3ohbu)AVTK(ac)VQK | 61 |
| H2B | 24 | AVTK(ac)VQK(3ohbu)K | 62 |
| H3 | 10 | K(3ohbu)STGGK(ac)APR | 63 |
| H3 | 19, 24 | K(3ohbu)QLATK(3ohbu)AAR | 29 |
| H3 | 19 | K(3ohbu)QLATK(ac)AAR | 29 |
| H3 | 42 | YQK(3ohbu)STELLVR | 102 |
| H3 | 24 | QLATK(3ohbu)AAR | 64 |
| H3 | 28 | K(3ohbu)SAPATGGVK | 65 |
| H3 | 57 | YQK(3ohbu)STELLIR | 66 |
| H3 | 123 | VTIMPK(3ohbu)DIQLAR | 67 |
| H3 | 28 | K(3ohbu)SAPSTGGVK | 68 |
| H3 | 80 | EIAQDFK(3ohbu)TDLR | 69 |
| H4 | 9 | GGK(3ohbu)GLGK | 70 |
| H4 | 13 | GLGK(3ohbu)GGAK(ac)R | 71 |
| H4 | 32 | DNIQGITK(3ohbu)PAIR | 72 |
| H4 | 78 | DAVTYTEHAK(3ohbu)R | 73 |
| H4 | 92 | TVTAMDVVYALK(3ohbu)R | 74 |

TABLE 2

List of histone K3ohbu sites identified from the livers of female C57BL/6 mice with 48 hrs starvation or C57BKS/J db/db mice treated with streptozotocin (200 mg/kg body weight) for 48 hrs. "K(3ohbu)" and "K(ac)" indicates 3-hydroxybutyrylated and acetylated lysine, respectively.

| Mouse histone protein | Position | Peptide Sequence | SEQ ID NO |
|---|---|---|---|
| H1 | 34 | K(3ohbu)ASGPPVSELITK | 38 |
| H1 | 34 | K(3ohbu)TSGPPVSELITK | 75 |
| H1 | 46 | TSGPPVSELITK(3ohbu)AVAASK | 76 |
| H1 | 52 | AVAASK(3ohbu)ER | 77 |
| H1 | 64 | K(3ohbu)ALAAGGYDVEK | 78 |
| H1 | 64 | K(3ohbu)ALAAAGYDVEK | 40 |
| H1 | 82 | LVTTGVLK(3ohbu)QTK | 79 |
| H1 | 85 | LGLK(3ohbu)SLVSK | 35 |
| H1 | 90 | SLVSK(3ohbu)GTLVQTK | 36 |
| H1 | 97 | GTLVQTK(3ohbu)GTGASGSFK | 41 |
| H1 | 106 | GTGASGSFK(3ohbu)LNK | 37 |
| H1 | 164 | VVK(3ohbu)VKPVK | 80 |
| H2A | 12 | AGGK(ac)AGK(ac)DSGK(3ohbu)AK | 81 |
| H2A | 14 | AGK(ac)DSGK(ac)AK(3ohbu)TK | 82 |
| H2A | 96 | NDEELNK(3ohbu)LLGK | 51 |
| H2A | 96 | NDEELNK(3ohbu)LLGR | 83 |
| H2A | 116 | ATIAGGGVIPHIHK(3ohbu)SLIGK | 84 |
| H2A | 119 | VTIAQGGVLPNIQAVLLPK(3ohbu)K | 52 |
| H2A | 128 | SSATVGPK(3ohbu)APAVGK | 85 |
| H2A | 134 | APAVGK(3ohbu)K | 86 |
| H2B | 6 | PEPTK(3ohbu)SAPAPK | 53 |
| H2B | 6 | PDPAK(3ohbu)SAPAPK | 87 |
| H2B | 6 | PELAK(3ohbu)SAPAPK | 60 |
| H2B | 12 | SAPAPK(ac)K(3ohbu)GSK(ac)K | 88 |
| H2B | 12 | SAPAPK(3ohbu)K(ac)GSK(ac)K(ac)AISK | 89 |
| H2B | 12 | PEPAK(ac)SAPAPK(3ohbu)K(ac)GSK | 90 |
| H2B | 13 | SAPAPK(ac)K(3ohbu)GSK(ac)K(ac)AVTK(ac)AQK | 91 |
| H2B | 16 | K(ac)GSK(3ohbu)K(ac)AISK | 92 |
| H2B | 16 | SAPAPK(ac)K(ac)GSK(3ohbu)K | 88 |
| H2B | 16 | K(ac)GSK(ac)K(3ohbu)AVTK(ac)AQK | 93 |
| H2B | 17 | K(ac)GSK(ac)K(3ohbu)AVTK | 94 |
| H2B | 21 | K(ac)GSK(ac)K(ac)ALTK(3ohbu)AQK | 95 |
| H2B | 21 | K(ac)AVTK(3ohbu)AQK(ac)K | 96 |
| H2B | 24 | AVTK(ac)VQK(3ohbu)K | 62 |
| H2B | 24 | K(ac)GSK(ac)K(ac)AISK(ac)AQK(3ohbu)K | 97 |

TABLE 2-continued

List of histone K3ohbu sites identified from the livers of female C57BL/6 mice with 48 hrs starvation or C57BKS/J db/db mice treated with streptozotocin (200 mg/kg body weight) for 48 hrs. "K(3ohbu)" and "K(ac)" indicates 3-hydroxybutyrylated and acetylated lysine, respectively.

| Mouse histone protein | Position | Peptide Sequence | SEQ ID NO |
|---|---|---|---|
| H2B | 35 | K(3ohbu)ESYSVYVYK | 57 |
| H2B | 109 | LLLPGELAK(3ohbu)HAVSEGTK | 98 |
| H2B | 117 | HAVSEGTK(3ohbu)AVTK | 58 |
| H3 | 10 | K(ac)STGGK(3ohbu)APR | 63 |
| H3 | 19 | K(3ohbu)QLATK | 99 |
| H3 | 24 | QLATK(3ohbu)AAR | 64 |
| H3 | 24 | K(ac)QLATK(3ohbu)AAR | 29 |
| H3 | 80 | EIAQDFK(3ohbu)TDLR | 69 |
| H3 | 57 | YQK(3ohbu)STELLIR | 66 |
| H3 | 123 | VTIM(ox)PK(3ohbu)DIQLAR | 67 |
| H4 | 6 | GK(3ohbu)GGKGLGK(ac)GGAK(ac)R | 100 |
| H4 | 9 | GGK(3ohbu)GLGK | 70 |
| H4 | 13 | GLGK(3ohbu)GGAK | 101 |

TABLE 3

List of the sequences in FIG. 4d

| Sequence | SEQ ID NO |
|---|---|
| SSSSSSKLSKSSK | 114 |
| KKAPPSKTGSKRR | 115 |
| GPGKLSKAAALAS | 116 |
| ATPAASKSEPVQA | 117 |
| LKSLVSKGTLVQT | 118 |
| KAVAASKERSGVS | 119 |
| APKKGSKKAITKA | 120 |
| APKKGSKKAVTKA | 121 |
| KAVAASKERNGLS | 122 |
| IKSLVSKGTLVQT | 123 |
| KSKPKRKSTPKSA | 124 |
| APSKPGKASPSAR | 125 |
| PTPALPKLGPVPP | 126 |
| SLTRSKKQQPATV | 127 |
| GRRTVKKTLPPKE | 128 |
| LAAVAQKKRPLVS | 129 |
| LVESTAKGLPRRK | 130 |
| ATKAARKSAPSTG | 131 |
| QKGERLKNYPGRL | 132 |
| VELGNLKNRPGEL | 133 |
| KSKPAKKAAAAKA | 134 |
| AAGSLAKLASSRS | 135 |
| SGLAQPKGAPKTK | 136 |
| EKTKTTKSAVLAR | 137 |
| VPSRKLKTAEREP | 138 |
| RVATQGKKAKVQQ | 139 |
| GQPQTRKQATPVL | 140 |
| LPGELAKHAVSEG | 141 |
| TPKKAKKPAAATV | 142 |
| NIQGITKPAIRRL | 143 |
| GKSKGGKFGKKKK | 144 |
| SSGSKQKGGFSGG | 145 |
| AGKLLLKAGAGTS | 146 |
| RTRGVTKTGRTVT | 147 |
| ERLEAKKLGVPSE | 148 |

TABLE 3-continued

List of the sequences in FIG. 4d

| Sequence | SEQ ID NO |
| --- | --- |
| TXTTTRKVGQRAL | 149 |
| LPGELAKDGVSEG | 150 |
| KSAPAPKKGSKKA | 151 |
| MAKKVTKAGGSAA | 152 |
| AGKGLGKGGAKCH | 153 |

What is claimed:

1. A method for detecting a 3-hydroxybutyrylated lysine in a protein or a fragment thereof, comprising:
   (a) immunizing a host with an isolated peptide comprising a 3-hydroxybutyrylated lysine, whereby an affinity reagent that binds specifically to the peptide is produced,
   (b) contacting the protein or a fragment thereof with the affinity reagent, whereby the affinity reagent and the protein or a fragment thereof forms a binding complex, and
   (c) detecting the binding complex, wherein the presence of the binding complex indicates the presence of a 3-hydroxybutyrylated lysine in the protein or a fragment thereof.

2. The method of claim 1, wherein the peptide comprises an amino acid sequence selected from the group consisting of K(3ohbu)QLATK(3ohbu)AAR (SEQ ID NO: 29 in which the residues at positions 1 and 6 are each a 3-hydroxybutyrylated lysine), K(3ohbu)QLATK(ac)AAR (SEQ ID NO: 29 in which the residue at position 1 is a 3-hydroxybutyrylated lysine and the residue at position 6 is an acetylated lysine), K(ac)QLATK(3ohbu)AAR (SEQ ID NO: 29 in which and the residue at position 1 is an acetylated lysine and the residue at position 6 is a 3-hydroxybutyrylated lysine), K(3ohbu)LAATPK (SEQ ID NO: 30), VTK(3ohbu)AGGSAALSPSK (SEQ ID NO: 31), AGGSAALSPSK(3ohbu)K (SEQ ID NO: 32), GAPAAATAPAPTAHK(3ohbu)AK (SEQ ID NO: 33), PSVPK(3ohbu)VPK (SEQ ID NO: 34), LGLK(3ohbu)SLVSK (SEQ ID NO: 35), SLVSK(3ohbu)GTLVQTK (SEQ ID NO: 36), GTGASGSFK(3ohbu)LNK (SEQ ID NO: 37), K(3ohbu)ASGPPVSELITK (SEQ ID NO: 38), ASGPPVSELITK(3ohbu)AVAASK (SEQ ID NO: 39), K(3ohbu)ALAAAGYDVEK (SEQ ID NO: 40), GTLVQTK(3ohbu)GTGASGSFK (SEQ ID NO: 41), ALAAAGYDVEK(3ohbu)NNSR (SEQ ID NO: 42), K(3ohbu)PAAATVTK (SEQ ID NO: 43), AGGK(3ohbu)AGK(ac)DSGK (SEQ ID NO: 44), AGK(ac)DSGK(3ohbu)AK (SEQ ID NO: 45), K(3ohbu)TSATVGPK (SEQ ID NO: 46), TSATVGPK(3ohbu)APSGGK(ac)K (SEQ ID NO: 47), K(3ohbu)ATQASQEY (SEQ ID NO: 48), GK(3ohbu)LEAIITPPPAK (SEQ ID NO: 49), K(3ohbu)GNYAER (SEQ ID NO: 50), NDEELNK(3ohbu)LLGK (SEQ ID NO: 51), VTIAQGGVLPNIQAVLLPK(3ohbu)K (SEQ ID NO: 52), PEPTK(3ohbu)SAPAPK (SEQ ID NO: 53), SAPAPK(3ohbu)K(ac)GSK (SEQ ID NO: 54), GSK(ac)K(3ohbu)AVTK (SEQ ID NO: 55), AVTK(3ohbu)AQK (SEQ ID NO: 56), K(3ohbu)ESYSVYVYK (SEQ ID NO: 57), HAVSEGTK(3ohbu)AVTK (SEQ ID NO: 58), AVTK(3ohbu)YTSSK (SEQ ID NO: 59), PELAK(3ohbu)SAPAPK (SEQ ID NO: 60), K(3ohbu)AVTK(ac)VQK (SEQ ID NO: 61), AVTK(ac)VQK(3ohbu)K (SEQ ID NO: 62), K(3ohbu)STGGK(ac)APR (SEQ ID NO: 63 in which the residue at position 1 is a 3-hydroxybutyrylated lysine and the residue at position 6 is an acetylated lysine), K(ac)STGGK(3ohbu)APR (SEQ ID NO: 63 in which the residue at position 1 is an acetylated lysine and the residue at position 6 is a 3-hydroxybutyrylated lysine), QLATK(3ohbu)AAR (SEQ ID NO: 64), K(3ohbu)SAPATGGVK (SEQ ID NO: 65), YQK(3ohbu)STELLIR (SEQ ID NO: 66), VTIMPK(3ohbu)DIQLAR (SEQ ID NO: 67 in which the residue at position 6 is a 3-hydroxybutyrylated lysine), VTIM(ox)PK(3ohbu)DIQLAR (SEQ ID NO: 67 in which the residue at position 4 is an oxidized methionine and the residue at position 6 is a 3-hydroxybutyrylated lysine), K(3ohbu)SAPSTGGVK (SEQ ID NO: 68), EIAQDFK(3ohbu)TDLR (SEQ ID NO: 69), GGK(3ohbu)GLGK (SEQ ID NO: 70), GLGK(3ohbu)GGAK(ac)R (SEQ ID NO: 71), DNIQGITK(3ohbu)PAIR (SEQ ID NO: 72), DAVTYTEHAK(3ohbu)R (SEQ ID NO: 73), TVTAMDVVYALK(3ohbu)R (SEQ ID NO: 74), K(3ohbu)TSGPPVSELITK (SEQ ID NO: 75), TSGPPVSELITK(3ohbu)AVAASK (SEQ ID NO: 76), AVAASK(3ohbu)ER (SEQ ID NO: 77), K(3ohbu)ALAAGGYDVEK (SEQ ID NO: 78), LVTTGVLK(3ohbu)QTK (SEQ ID NO: 79), VVK(3ohbu)VKPVK (SEQ ID NO: 80), AGGK(ac)AGK(ac)DSGK(3ohbu)AK (SEQ ID NO: 81), AGK(ac)DSGK(ac)AK(3ohbu)TK (SEQ ID NO: 82), NDEELNK(3ohbu)LLGR (SEQ ID NO: 83), ATIAGGGVIPHIHK(3ohbu)SLIGK (SEQ ID NO: 84), SSATVGPK(3ohbu)APAVGK (SEQ ID NO: 85), APAVGK(3ohbu)K (SEQ ID NO: 86), PDPAK(3ohbu)SAPAPK (SEQ ID NO: 87), SAPAPK(ac)K(3ohbu)GSK(ac)K (SEQ ID NO: 88 in which the residues at positions 6 and 10 are each a 3-hydroxybutyrylated lysine and the residue at position 7 is an acetylated lysine), SAPAPK(ac)K(ac)GSK(3ohbu)K (SEQ ID NO: 88 in which the residues at positions 6 and 7 are each an acetylated lysine and the residue at position 10 is a 3-hydroxybutyrylated lysine), SAPAPK(3ohbu)K(ac)GSK(ac)K(ac)AISK (SEQ ID NO: 89), PEPAK(ac)SAPAPK(3ohbu)K(ac)GSK (SEQ ID NO: 90), SAPAPK(ac)K(3ohbu)GSK(ac)K(ac)AVTK(ac)AQK (SEQ ID NO:91), K(ac)GSK(3ohbu)K(ac)AISK (SEQ ID NO: 92), K(ac)GSK(ac)K(3ohbu)AVTK(ac)AQK (SEQ ID NO: 93), K(ac)GSK(ac)K(3ohbu)AVTK (SEQ ID NO: 94), K(ac)GSK(ac)K(ac)ALTK(3ohbu)AQK (SEQ ID NO: 95), K(ac)AVTK(3ohbu)AQK(ac)K (SEQ ID NO: 96), K(ac)GSK(ac)K(ac)AISK(ac)AQK(3ohbu)K (SEQ ID NO: 97), LLLPGELAK(3ohbu)HAVSEGTK (SEQ ID NO: 98), K(3ohbu)QLATK (SEQ ID NO: 99), GK(3ohbu)GGKGLGK(ac)GGAK(ac)R (SEQ ID NO: 100), GLGK(3ohbu)GGAK (SEQ ID NO: 101) and YQK(3ohbu)STELLVR (SEQ ID NO: 102).

3. The method of claim 1, wherein the peptide consists of an amino acid sequence selected from the group consisting of K(3ohbu)QLATK(3ohbu)AAR (SEQ ID NO: 29 in which the residues at positions 1 and 6 are each a 3-hydroxybutyrylated lysine), K(3ohbu)QLATK(ac)AAR (SEQ ID NO: 29 in which the residue at position 1 is a 3-hydroxybutyrylated lysine and the residue at position 6 is an acetylated lysine), K(ac)QLATK(3ohbu)AAR (SEQ ID NO: 29 in which the residue at position 1 is an acetylated lysine and the residue at position 6 is a 3-hydroxybutyrylated lysine), K(3ohbu)LAATPK (SEQ ID NO: 30), VTK(3ohbu)AGGSAALSPSK (SEQ ID NO: 31), AGGSAALSPSK(3ohbu)K (SEQ ID NO: 32), GAPAAATAPAPTAHK(3ohbu)AK (SEQ ID NO: 33), PSVPK(3ohbu)VPK (SEQ ID NO: 34), LGLK(3ohbu)SLVSK (SEQ ID NO: 35), SLVSK(3ohbu)GTLVQTK (SEQ ID NO: 36), GTGASGSFK(3ohbu)LNK (SEQ ID NO: 37), K(3ohbu)ASGPPVSELITK (SEQ ID NO: 38), ASGPPVSELITK(3ohbu)AVAASK (SEQ ID NO: 39), K(3ohbu)ALAAAGYDVEK (SEQ ID NO: 40), GTLVQTK(3ohbu)GTGASGSFK (SEQ ID NO: 41), ALAAAGYDVEK(3ohbu)NNSR (SEQ ID NO: 42), K(3ohbu)PAAATVTK (SEQ ID NO: 43), AGGK(3ohbu)AGK(ac)DSGK (SEQ ID NO: 44), AGK(ac)DSGK(3ohbu)AK (SEQ ID NO: 45), K(3ohbu)TSATVGPK (SEQ ID NO: 46), TSATVGPK(3ohbu)APSGGK(ac)K (SEQ ID NO: 47), K(3ohbu)ATQASQEY (SEQ ID NO: 48), GK(3ohbu)LEAIITPPPAK (SEQ ID NO: 49), K(3ohbu)GNYAER (SEQ ID NO: 50), NDEELNK(3ohbu)LLGK (SEQ ID NO: 51), VTIAQGGVLPNIQAVLLPK(3ohbu)K (SEQ ID NO: 52), PEPTK(3ohbu)SAPAPK (SEQ ID NO: 53), SAPAPK(3ohbu)K(ac)GSK (SEQ ID NO: 54), GSK(ac)K(3ohbu)AVTK (SEQ ID NO: 55), AVTK(3ohbu)AQK (SEQ ID NO: 56), K(3ohbu)ESYSVYVYK (SEQ ID NO: 57), HAVSEGTK(3ohbu)AVTK (SEQ ID NO: 58), AVTK(3ohbu)YTSSK (SEQ ID NO: 59), PELAK(3ohbu)SAPAPK (SEQ ID NO: 60), K(3ohbu)AVTK(ac)VQK (SEQ ID NO: 61), AVTK(ac)VQK(3ohbu)K (SEQ ID NO: 62), K(3ohbu)STGGK(ac)APR (SEQ ID NO: 63 in which the residue at position 1 is a 3-hydroxybutyrylated lysine and the residue at position 6 is an acetylated lysine), K(ac)STGGK(3ohbu)APR (SEQ ID NO: 63 in which the residue at position 1 is an acetylated lysine and the residue at position 6 is a 3-hydroxybutyrylated lysine), QLATK(3ohbu)AAR (SEQ ID NO: 64), K(3ohbu)SAPATGGVK (SEQ ID NO: 65), YQK(3ohbu)STELLIR (SEQ ID NO: 66), VTIMPK(3ohbu)DIQLAR (SEQ ID NO: 67 in which the residue at position 6 is a 3-hydroxybutyrylated lysine), VTIM(ox)PK(3ohbu)DIQLAR (SEQ ID NO: 67 in which the residue at position 4 is an oxidized methionine and the residue at position 6 is a 3-hydroxybutyrylated lysine), K(3ohbu)SAPSTGGVK (SEQ ID NO: 68), EIAQDFK(3ohbu)TDLR (SEQ ID NO: 69), GGK(3ohbu)GLGK (SEQ ID NO: 70), GLGK(3ohbu)GGAK(ac)R (SEQ ID NO: 71), DNIQGITK(3ohbu)PAIR (SEQ ID NO: 72), DAVTYTEHAK(3ohbu)R (SEQ ID NO: 73), TVTAMDVVYALK(3ohbu)R (SEQ ID NO: 74), K(3ohbu)TSGPPVSELITK (SEQ ID NO: 75), TSGPPVSELITK(3ohbu)AVAASK (SEQ ID NO: 76), AVAASK(3ohbu)ER (SEQ ID NO: 77), K(3ohbu)ALAAGGYDVEK (SEQ ID NO: 78), LVTTGVLK(3ohbu)QTK (SEQ ID NO: 79), VVK(3ohbu)VKPVK (SEQ ID NO: 80), AGGK(ac)AGK(ac)DSGK(3ohbu)AK (SEQ ID NO: 81), AGK(ac)DSGK(ac)AK(3ohbu)TK (SEQ ID NO: 82), NDEELNK(3ohbu)LLGR (SEQ ID NO: 83), ATIAGGGVIPHIHK(3ohbu)SLIGK (SEQ ID NO: 84), SSATVGPK(3ohbu)APAVGK (SEQ ID NO: 85), APAVGK(3ohbu)K (SEQ ID NO: 86), PDPAK(3ohbu)SAPAPK (SEQ ID NO: 87), SAPAPK(ac)K(3ohbu)GSK(ac)K (SEQ ID NO: 88 in which the residues at positions 6 and 10 are each a 3-hydroxybutyrylated lysine and the residue at position 7 is an acetylated lysine), SAPAPK(ac)K(ac)GSK(3ohbu)K (SEQ ID NO: 88 in which the residues at positions 6 and 7 are each an acetylated lysine and the residue at position 10 is a 3-hydroxybutyrylated lysine), SAPAPK(3ohbu)K(ac)GSK(ac)K(ac)AISK (SEQ ID NO: 89), PEPAK(ac)SAPAPK(3ohbu)K(ac)GSK (SEQ ID NO: 90), SAPAPK(ac)K(3ohbu)GSK(ac)K(ac)AVTK(ac)AQK (SEQ ID NO:91), K(ac)GSK(3ohbu)K(ac)AISK (SEQ ID NO: 92), K(ac)GSK(ac)K(3ohbu)AVTK(ac)AQK (SEQ ID NO: 93), K(ac)GSK(ac)K(3ohbu)AVTK (SEQ ID NO: 94), K(ac)GSK(ac)K(ac)ALTK(3ohbu)AQK (SEQ ID NO: 95), K(ac)AVTK(3ohbu)AQK(ac)K (SEQ ID NO: 96), K(ac)GSK(ac)K(ac)AISK(ac)AQK(3ohbu)K (SEQ ID NO: 97), LLLPGELAK(3ohbu)HAVSEGTK (SEQ ID NO: 98), K(3ohbu)QLATK (SEQ ID NO: 99), GK(3ohbu)GGKGLGK(ac)GGAK(ac)R (SEQ ID NO: 100), GLGK(3ohbu)GGAK (SEQ ID NO: 101) and YQK(3ohbu)STELLVR (SEQ ID NO: 102).

4. A method for detecting a 3-hydroxybutyrylated lysine in a protein or a fragment thereof, comprising:
 (a) screening a peptide library using an isolated peptide comprising a 3-hydroxybutyrylated lysine, whereby an affinity reagent that binds specifically to the peptide is produced,
 (b) contacting the protein or a fragment thereof with the affinity reagent, whereby the affinity reagent and the protein or a fragment thereof forms a binding complex, and (c) detecting the binding complex, wherein the presence of the binding complex indicates the presence of a 3-hydroxybutyrylated lysine in the protein or a fragment thereof.

5. The method of claim 4, wherein the peptide comprises an amino acid sequence selected from the group consisting of K(3ohbu)QLATK(3ohbu)AAR (SEQ ID NO: 29 in which the residues at positions 1 and 6 are each a 3-hydroxybutyrylated lysine), K(3ohbu)QLATK(ac)AAR (SEQ ID NO: 29 in which the residue at position 1 is a 3-hydroxybutyrylated lysine and the residue at position 6 is an acetylated lysine), K(ac)QLATK(3ohbu)AAR (SEQ ID NO: 29 in which and the residue at position 1 is an acetylated lysine and the residue at position 6 is a 3-hydroxybutyrylated lysine), K(3ohbu)LAATPK (SEQ ID NO: 30), VTK(3ohbu)AGGSAALSPSK (SEQ ID NO: 31), AGGSAALSPSK(3ohbu)K (SEQ ID NO: 32), GAPAAATAPAPTAHK(3ohbu)AK (SEQ ID NO: 33), PSVPK(3ohbu)VPK (SEQ ID NO: 34), LGLK(3ohbu)SLVSK (SEQ ID NO: 35), SLVSK(3ohbu)GTLVQTK (SEQ ID NO: 36), GTGASGSFK(3ohbu)LNK (SEQ ID NO: 37), K(3ohbu)ASGPPVSELITK (SEQ ID NO: 38), ASGPPVSELITK(3ohbu)AVAASK (SEQ ID NO: 39), K(3ohbu)ALAAAGYDVEK (SEQ ID NO: 40), GTLVQTK(3ohbu)GTGASGSFK (SEQ ID NO: 41), ALAAAGYDVEK(3ohbu)NNSR (SEQ ID NO: 42), K(3ohbu)PAAATVTK (SEQ ID NO: 43), AGGK(3ohbu)AGK(ac)DSGK (SEQ ID NO: 44), AGK(ac)DSGK(3ohbu)AK (SEQ ID NO: 45), K(3ohbu)TSATVGPK (SEQ ID NO: 46), TSATVGPK(3ohbu)APSGGK(ac)K (SEQ ID NO: 47), K(3ohbu)ATQASQEY (SEQ ID NO: 48), GK(3ohbu)LEAIITPPPAK (SEQ ID NO: 49), K(3ohbu)GNYAER (SEQ ID NO: 50), NDEELNK(3ohbu)LLGK (SEQ ID NO: 51), VTIAQGGVLPNIQAVLLPK(3ohbu)K (SEQ ID NO: 52), PEPTK(3ohbu)SAPAPK (SEQ ID NO: 53), SAPAPK(3ohbu)K(ac)GSK (SEQ ID NO: 54), GSK(ac)K(3ohbu)AVTK (SEQ ID NO: 55), AVTK(3ohbu)AQK (SEQ ID NO: 56), K(3ohbu)ESYSVYVYK (SEQ ID NO: 57), HAVSEGTK(3ohbu)AVTK (SEQ ID NO: 58), AVTK(3ohbu)YTSSK (SEQ ID NO: 59), PELAK(3ohbu)SAPAPK (SEQ ID NO: 60), K(3ohbu)AVTK(ac)VQK (SEQ ID NO: 61), AVTK(ac)VQK(3ohbu)K (SEQ ID NO: 62), K(3ohbu)STGGK(ac)APR (SEQ ID NO: 63 in which the residue at position 1 is a 3-hydroxybutyrylated lysine and the residue at position 6 is an acetylated lysine), K(ac)STGGK(3ohbu)APR (SEQ ID NO: 63 in which the residue at position 1 is an acetylated lysine and the residue at position 6 is a 3-hydroxybutyrylated lysine), QLATK(3ohbu)AAR (SEQ ID NO: 64), K(3ohbu)SAPATGGVK (SEQ ID NO: 65), YQK(3ohbu)STELLIR (SEQ ID NO: 66), VTIMPK(3ohbu)DIQLAR (SEQ ID NO: 67 in which the residue at position 6 is a 3-hydroxybutyrylated lysine), VTIM(ox)PK(3ohbu)DIQLAR (SEQ ID NO: 67 in which the residue at position 4 is an oxidized methionine and the residue at position 6 is a 3-hydroxybutyrylated lysine), K(3ohbu)SAPSTGGVK (SEQ ID NO: 68), EIAQDFK(3ohbu)TDLR (SEQ ID NO: 69), GGK(3ohbu)GLGK (SEQ ID NO: 70), GLGK(3ohbu)GGAK(ac)R (SEQ ID NO: 71), DNIQGITK(3ohbu)PAIR (SEQ ID NO: 72), DAVTYTEHAK(3ohbu)R (SEQ ID NO: 73), TVTAMDVVYALK(3ohbu)R (SEQ ID NO: 74), K(3ohbu)TSGPPVSELITK (SEQ ID NO: 75), TSGPPVSELITK(3ohbu)AVAASK (SEQ ID NO: 76), AVAASK(3ohbu)ER (SEQ ID NO: 77), K(3ohbu)ALAAGGYDVEK (SEQ ID NO: 78), LVTTGVLK(3ohbu)QTK (SEQ ID NO: 79), VVK(3ohbu)VKPVK (SEQ ID NO: 80), AGGK(ac)AGK(ac)DSGK(3ohbu)AK (SEQ ID NO: 81), AGK(ac)DSGK(ac)AK(3ohbu)TK (SEQ ID NO: 82), NDEELNK(3ohbu)LLGR (SEQ ID NO: 83), ATIAGGGVIPHIHK(3ohbu)SLIGK (SEQ ID NO: 84), SSATVGPK(3ohbu)APAVGK (SEQ ID NO: 85), APAVGK(3ohbu)K (SEQ ID NO: 86), PDPAK(3ohbu)SAPAPK (SEQ ID NO: 87), SAPAPK(ac)K(3ohbu)GSK(ac)K (SEQ ID NO: 88 in which the residues at positions 6 and 10 are each a 3-hydroxybutyrylated lysine and the residue at position 7 is an acetylated lysine), SAPAPK(ac)K(ac)GSK(3ohbu)K (SEQ ID NO: 88 in which the residues at positions 6 and 7 are each an acetylated lysine and the residue at position 10 is a 3-hydroxybutyrylated lysine), SAPAPK(3ohbu)K(ac)GSK(ac)K(ac)AISK (SEQ ID NO: 89), PEPAK(ac)SAPAPK(3ohbu)K(ac)GSK (SEQ ID NO: 90), SAPAPK(ac)K(3ohbu)GSK(ac)K(ac)AVTK(ac)AQK (SEQ ID NO:91), K(ac)GSK(3ohbu)K(ac)AISK (SEQ ID NO: 92), K(ac)GSK(ac)K(3ohbu)AVTK(ac)AQK (SEQ ID NO: 93), K(ac)GSK(ac)K(3ohbu)AVTK (SEQ ID NO: 94), K(ac)GSK(ac)K(ac)ALTK(3ohbu)AQK (SEQ ID NO: 95), K(ac)AVTK(3ohbu)AQK(ac)K (SEQ ID NO: 96), K(ac)GSK(ac)K(ac)AISK(ac)AQK(3ohbu)K (SEQ ID NO: 97), LLLPGELAK(3ohbu)HAVSEGTK (SEQ ID NO: 98), K(3ohbu)QLATK (SEQ ID NO: 99), GK(3ohbu)GGKGLGK(ac)GGAK(ac)R (SEQ ID NO: 100), GLGK(3ohbu)GGAK (SEQ ID NO: 101) and YQK(3ohbu)STELLVR (SEQ ID NO: 102).

6. The method of claim 4, wherein the peptide consists of an amino acid sequence selected from the group consisting of K(3ohbu)QLATK(3ohbu)AAR (SEQ ID NO: 29 in which the residues at positions 1 and 6 are each a 3-hydroxybutyrylated lysine), K(3ohbu)QLATK(ac)AAR (SEQ ID NO: 29 in which the residue at position 1 is a 3-hydroxybutyrylated lysine and the residue at position 6 is an acetylated lysine), K(ac)QLATK(3ohbu)AAR (SEQ ID NO: 29 in which and the residue at position 1 is an acetylated lysine and the residue at position 6 is a 3-hydroxybutyrylated lysine), K(3ohbu)LAATPK (SEQ ID NO: 30), VTK(3ohbu)AGGSAALSPSK (SEQ ID NO: 31), AGGSAALSPSK(3ohbu)K (SEQ ID NO: 32), GAPAAATAPAPTAHK(3ohbu)AK (SEQ ID NO: 33), PSVPK(3ohbu)VPK (SEQ ID NO: 34), LGLK(3ohbu)SLVSK (SEQ ID NO: 35), SLVSK(3ohbu)GTLVQTK (SEQ ID NO: 36), GTGASGSFK(3ohbu)LNK (SEQ ID NO: 37), K(3ohbu)ASGPPVSELITK (SEQ ID NO: 38), ASGPPVSELITK(3ohbu)AVAASK (SEQ ID NO: 39), K(3ohbu)ALAAAGYDVEK (SEQ ID NO: 40), GTLVQTK(3ohbu)GTGASGSFK (SEQ ID NO: 41), ALAAAGYDVEK(3ohbu)NNSR (SEQ ID NO: 42), K(3ohbu)PAAATVTK (SEQ ID NO: 43), AGGK(3ohbu)AGK(ac)DSGK (SEQ ID NO: 44), AGK(ac)DSGK(3ohbu)AK (SEQ ID NO: 45), K(3ohbu)TSATVGPK (SEQ ID NO: 46), TSATVGPK(3ohbu)APSGGK(ac)K (SEQ ID NO: 47), K(3ohbu)ATQASQEY (SEQ ID NO: 48), GK(3ohbu)LEAIITPPPAK (SEQ ID NO: 49), K(3ohbu)GNYAER (SEQ ID NO: 50), NDEELNK(3ohbu)LLGK (SEQ ID NO: 51), VTIAQGGVLPNIQAVLLPK(3ohbu)K (SEQ ID NO: 52), PEPTK(3ohbu)SAPAPK (SEQ ID NO: 53), SAPAPK(3ohbu)K(ac)GSK (SEQ ID NO: 54), GSK(ac)K(3ohbu)AVTK (SEQ ID NO: 55), AVTK(3ohbu)AQK (SEQ ID NO: 56), K(3ohbu)ESYSVYVYK (SEQ ID NO: 57), HAVSEGTK(3ohbu)AVTK (SEQ ID NO: 58), AVTK(3ohbu)YTSSK (SEQ ID NO: 59), PELAK(3ohbu)SAPAPK (SEQ ID NO: 60), K(3ohbu)AVTK(ac)VQK (SEQ ID NO: 61), AVTK(ac)VQK(3ohbu)K (SEQ ID NO: 62), K(3ohbu)STGGK(ac)APR (SEQ ID NO: 63 in which the residue at position 1 is a 3-hydroxybutyrylated lysine and the residue at position 6 is an acetylated lysine), K(ac)STGGK(3ohbu)APR (SEQ ID NO: 63 in which the residue at position 1 is an acetylated lysine and the residue at position 6 is a 3-hydroxybutyrylated lysine), QLATK(3ohbu)AAR (SEQ ID NO: 64), K(3ohbu)SAPATGGVK (SEQ ID NO: 65), YQK(3ohbu)STELLIR (SEQ ID NO: 66), VTIMPK(3ohbu)DIQLAR (SEQ ID NO: 67 in which the residue at position 6 is a 3-hydroxybutyrylated lysine), VTIM(ox)PK(3ohbu)DIQLAR (SEQ ID NO: 67 in which the residue at position 4 is an oxidized methionine and the residue at position 6 is a 3-hydroxybutyrylated lysine), K(3ohbu)SAPSTGGVK (SEQ ID NO: 68), EIAQDFK(3ohbu)TDLR (SEQ ID NO: 69), GGK(3ohbu)GLGK (SEQ ID NO: 70), GLGK(3ohbu)GGAK(ac)R (SEQ ID NO: 71), DNIQGITK(3ohbu)PAIR (SEQ ID NO: 72), DAVTYTEHAK(3ohbu)R (SEQ ID NO: 73), TVTAMDVVYALK(3ohbu)R (SEQ ID NO: 74), K(3ohbu)TSGPPVSELITK (SEQ ID NO: 75), TSGPPVSELITK(3ohbu)AVAASK (SEQ ID NO: 76), AVAASK(3ohbu)ER (SEQ ID NO: 77), K(3ohbu)ALAAGGYDVEK (SEQ ID NO: 78), LVTTGVLK(3ohbu)QTK (SEQ ID NO: 79), VVK(3ohbu)VKPVK (SEQ ID NO: 80), AGGK(ac)AGK(ac)DSGK(3ohbu)AK (SEQ ID NO: 81), AGK(ac)DSGK(ac)AK(3ohbu)TK (SEQ ID NO: 82), NDEELNK(3ohbu)LLGR (SEQ ID NO: 83), ATIAGGGVIPHIHK(3ohbu)SLIGK (SEQ ID NO: 84), SSATVGPK(3ohbu)APAVGK (SEQ ID NO: 85), APAVGK(3ohbu)K (SEQ ID NO: 86), PDPAK(3ohbu)SAPAPK (SEQ ID NO: 87), SAPAPK(ac)K(3ohbu)GSK(ac)K (SEQ ID NO: 88 in which the residues at positions 6 and 10 are each a 3-hydroxybutyrylated lysine and the residue at position 7 is an acetylated lysine), SAPAPK(ac)K(ac)GSK(3ohbu)K (SEQ ID NO: 88 in which the residues at positions 6 and 7 are each an acetylated lysine and the residue at position 10 is a 3-hydroxybutyrylated lysine), SAPAPK(3ohbu)K(ac)GSK(ac)K(ac)AISK (SEQ ID NO: 89), PEPAK(ac)SAPAPK(3ohbu)K(ac)GSK (SEQ ID NO: 90), SAPAPK(ac)K(3ohbu)GSK(ac)K(ac)AVTK(ac)AQK (SEQ ID NO:91), K(ac)GSK(3ohbu)K(ac)AISK (SEQ ID NO: 92), K(ac)GSK(ac)K(3ohbu)AVTK(ac)AQK (SEQ ID NO: 93), K(ac)GSK(ac)K(3ohbu)AVTK (SEQ ID NO: 94), K(ac)GSK(ac)K(ac)ALTK(3ohbu)AQK (SEQ ID NO: 95), K(ac)AVTK(3ohbu)AQK(ac)K (SEQ ID NO: 96), K(ac)GSK(ac)K(ac)AISK(ac)AQK(3ohbu)K (SEQ ID NO: 97), LLLPGELAK(3ohbu)HAVSEGTK (SEQ ID NO: 98), K(3ohbu)QLATK (SEQ ID NO: 99), GK(3ohbu)GGKGLGK(ac)GGAK(ac)R (SEQ ID NO: 100), GLGK(3ohbu)GGAK (SEQ ID NO: 101) and YQK(3ohbu)STELLVR (SEQ ID NO: 102).

\* \* \* \* \*

SEQUENCE LISTING

<160> NUMBER OF SEQ ID NOS: 153

<210> SEQ ID NO 1
<211> LENGTH: 213
<212> TYPE: PRT
<213> ORGANISM: Homo sapiens

<400> SEQUENCE: 1

```
Met Ser Glu Thr Ala Pro Ala Ala Pro Ala Ala Ala Pro Ala Glu
1               5                   10                  15

Lys Ala Pro Val Lys Lys Lys Ala Ala Lys Lys Ala Gly Gly Thr Pro
            20                  25                  30

Arg Lys Ala Ser Gly Pro Pro Val Ser Glu Leu Ile Thr Lys Ala Val
            35                  40                  45

Ala Ala Ser Lys Glu Arg Ser Gly Val Ser Leu Ala Ala Leu Lys Lys
50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Val Lys Lys Ala Gly Gly Thr Lys Pro
            115                 120                 125

Lys Lys Pro Val Gly Ala Ala Lys Lys Pro Lys Lys Ala Ala Gly Gly
130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
            180                 185                 190

Val Lys Pro Lys Ala Ala Lys Pro Lys Val Val Lys Pro Lys Lys Ala
            195                 200                 205

Ala Pro Lys Lys Lys
210
```

<210> SEQ ID NO 2
<211> LENGTH: 130
<212> TYPE: PRT
<213> ORGANISM: Homo sapiens

<400> SEQUENCE: 2

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30
```

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
 50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Lys Val Thr Ile Ala Gln Gly Gly Val Leu Pro Asn Ile
                100                 105                 110

Gln Ala Val Leu Leu Pro Lys Lys Thr Glu Ser His His Lys Ala Lys
                115                 120                 125

Gly Lys
    130

<210> SEQ ID NO 3
<211> LENGTH: 126
<212> TYPE: PRT
<213> ORGANISM: Homo sapiens

<400> SEQUENCE: 3

Met Pro Glu Pro Ser Lys Ser Ala Pro Ala Pro Lys Lys Gly Ser Lys
 1               5                  10                  15

Lys Ala Ile Thr Lys Ala Gln Lys Lys Asp Gly Lys Lys Arg Lys Arg
                 20                  25                  30

Ser Arg Lys Glu Ser Tyr Ser Ile Tyr Val Tyr Lys Val Leu Lys Gln
            35                  40                  45

Val His Pro Asp Thr Gly Ile Ser Ser Lys Ala Met Gly Ile Met Asn
 50                  55                  60

Ser Phe Val Asn Asp Ile Phe Glu Arg Ile Ala Gly Glu Ala Ser Arg
 65                  70                  75                  80

Leu Ala His Tyr Asn Lys Arg Ser Thr Ile Thr Ser Arg Glu Ile Gln
                 85                  90                  95

Thr Ala Val Arg Leu Leu Leu Pro Gly Glu Leu Ala Lys His Ala Val
                100                 105                 110

Ser Glu Gly Thr Lys Ala Val Thr Lys Tyr Thr Ser Ser Lys
                115                 120                 125

<210> SEQ ID NO 4
<211> LENGTH: 136
<212> TYPE: PRT
<213> ORGANISM: Homo sapiens

<400> SEQUENCE: 4

Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ser
                 20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
 50                  55                  60

Lys Leu Pro Phe Gln Arg Leu Val Arg Glu Ile Ala Gln Asp Phe Lys
 65                  70                  75                  80

Thr Asp Leu Arg Phe Gln Ser Ala Ala Ile Gly Ala Leu Gln Glu Ala
                 85                  90                  95

```
Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
130                 135

<210> SEQ ID NO 5
<211> LENGTH: 103
<212> TYPE: PRT
<213> ORGANISM: Homo sapiens

<400> SEQUENCE: 5

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 6
<211> LENGTH: 212
<212> TYPE: PRT
<213> ORGANISM: Mus musculus

<400> SEQUENCE: 6

Met Ser Glu Ala Ala Pro Ala Ala Pro Ala Ala Ala Pro Pro Ala Glu
1               5                   10                  15

Lys Ala Pro Ala Lys Lys Lys Ala Ala Lys Lys Pro Ala Gly Val Arg
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Ile Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Gln Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ala Ala Lys Lys Thr Pro Lys Lys Ala Lys Lys
145                 150                 155                 160

Pro Ala Ala Ala Ala Val Thr Lys Lys Val Ala Lys Ser Pro Lys Lys
                165                 170                 175
```

Ala Lys Val Thr Lys Pro Lys Val Lys Ser Ala Ser Lys Ala Val
            180                 185                 190

Lys Pro Lys Ala Ala Lys Pro Lys Val Ala Lys Ala Lys Val Ala
            195                 200                 205

Ala Lys Lys Lys
        210

<210> SEQ ID NO 7
<211> LENGTH: 130
<212> TYPE: PRT
<213> ORGANISM: Mus musculus

<400> SEQUENCE: 7

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 8
<211> LENGTH: 126
<212> TYPE: PRT
<213> ORGANISM: Mus musculus

<400> SEQUENCE: 8

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Ser Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 9

```
<211> LENGTH: 136
<212> TYPE: PRT
<213> ORGANISM: Mus musculus

<400> SEQUENCE: 9
```

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

```
<210> SEQ ID NO 10
<211> LENGTH: 103
<212> TYPE: PRT
<213> ORGANISM: Mus musculus

<400> SEQUENCE: 10
```

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

```
<210> SEQ ID NO 11
<211> LENGTH: 132
<212> TYPE: PRT
<213> ORGANISM: Saccharomyces cerevisiae

<400> SEQUENCE: 11
```

Met Ser Gly Gly Lys Gly Gly Lys Ala Gly Ser Ala Ala Lys Ala Ser
1               5                   10                  15

Gln Ser Arg Ser Ala Lys Ala Gly Leu Thr Phe Pro Val Gly Arg Val
            20                  25                  30

His Arg Leu Leu Arg Arg Gly Asn Tyr Ala Gln Arg Ile Gly Ser Gly
        35                  40                  45

```
Ala Pro Val Tyr Leu Thr Ala Val Leu Glu Tyr Leu Ala Ala Glu Ile
    50                  55                  60

Leu Glu Leu Ala Gly Asn Ala Ala Arg Asp Asn Lys Lys Thr Arg Ile
65                  70                  75                  80

Ile Pro Arg His Leu Gln Leu Ala Ile Arg Asn Asp Asp Glu Leu Asn
                85                  90                  95

Lys Leu Leu Gly Asn Val Thr Ile Ala Gln Gly Gly Val Leu Pro Asn
            100                 105                 110

Ile His Gln Asn Leu Leu Pro Lys Lys Ser Ala Lys Ala Thr Lys Ala
        115                 120                 125

Ser Gln Glu Leu
    130
```

<210> SEQ ID NO 12
<211> LENGTH: 131
<212> TYPE: PRT
<213> ORGANISM: Saccharomyces cerevisiae

<400> SEQUENCE: 12

```
Met Ser Ser Ala Ala Glu Lys Lys Pro Ala Ser Lys Ala Pro Ala Glu
1               5                   10                  15

Lys Lys Pro Ala Ala Lys Lys Thr Ser Thr Ser Val Asp Gly Lys Lys
                20                  25                  30

Arg Ser Lys Val Arg Lys Glu Thr Tyr Ser Ser Tyr Ile Tyr Lys Val
            35                  40                  45

Leu Lys Gln Thr His Pro Asp Thr Gly Ile Ser Gln Lys Ser Met Ser
    50                  55                  60

Ile Leu Asn Ser Phe Val Asn Asp Ile Phe Glu Arg Ile Ala Thr Glu
65                  70                  75                  80

Ala Ser Lys Leu Ala Ala Tyr Asn Lys Lys Ser Thr Ile Ser Ala Arg
                85                  90                  95

Glu Ile Gln Thr Ala Val Arg Leu Ile Leu Pro Gly Glu Leu Ala Lys
            100                 105                 110

His Ala Val Ser Glu Gly Thr Arg Ala Val Thr Lys Tyr Ser Ser Ser
        115                 120                 125

Thr Gln Ala
    130
```

<210> SEQ ID NO 13
<211> LENGTH: 136
<212> TYPE: PRT
<213> ORGANISM: Saccharomyces cerevisiae

<400> SEQUENCE: 13

```
Met Ala Arg Thr Lys Gln Thr Ala Arg Lys Ser Thr Gly Gly Lys Ala
1               5                   10                  15

Pro Arg Lys Gln Leu Ala Ser Lys Ala Ala Arg Lys Ser Ala Pro Ser
                20                  25                  30

Thr Gly Gly Val Lys Lys Pro His Arg Tyr Lys Pro Gly Thr Val Ala
            35                  40                  45

Leu Arg Glu Ile Arg Arg Phe Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Ile Gly Ala Leu Gln Glu Ser
                85                  90                  95
```

-continued

Val Glu Ala Tyr Leu Val Ser Leu Phe Glu Asp Thr Asn Leu Ala Ala
            100                 105                 110

Ile His Ala Lys Arg Val Thr Ile Gln Lys Lys Asp Ile Lys Leu Ala
        115                 120                 125

Arg Arg Leu Arg Gly Glu Arg Ser
        130                 135

<210> SEQ ID NO 14
<211> LENGTH: 103
<212> TYPE: PRT
<213> ORGANISM: Saccharomyces cerevisiae

<400> SEQUENCE: 14

Met Ser Gly Arg Gly Lys Gly Gly Lys Gly Leu Gly Lys Gly Gly Ala
1               5                   10                  15

Lys Arg His Arg Lys Ile Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Val Arg Ala Val Leu Lys Ser Phe Leu Glu
    50                  55                  60

Ser Val Ile Arg Asp Ser Val Thr Tyr Thr Glu His Ala Lys Arg Lys
65                  70                  75                  80

Thr Val Thr Ser Leu Asp Val Val Tyr Ala Leu Lys Arg Gln Gly Arg
                85                  90                  95

Thr Leu Tyr Gly Phe Gly Gly
            100

<210> SEQ ID NO 15
<211> LENGTH: 133
<212> TYPE: PRT
<213> ORGANISM: Tetrahymena thermophila

<400> SEQUENCE: 15

Met Ser Thr Thr Gly Lys Gly Lys Ala Lys Gly Lys Thr Ala Ser
1               5                   10                  15

Ser Lys Gln Val Ser Arg Ser Ala Arg Ala Gly Leu Gln Phe Pro Val
            20                  25                  30

Gly Arg Ile Ser Arg Phe Leu Lys Asn Gly Arg Tyr Ser Glu Arg Ile
        35                  40                  45

Gly Thr Gly Ala Pro Val Tyr Leu Ala Ala Val Leu Glu Tyr Leu Ala
    50                  55                  60

Ala Glu Val Leu Glu Leu Ala Gly Asn Ala Ala Lys Asp Asn Lys Lys
65                  70                  75                  80

Thr Arg Ile Val Pro Arg His Ile Leu Leu Ala Ile Arg Asn Asp Glu
                85                  90                  95

Glu Leu Asn Lys Leu Met Ala Asn Thr Thr Ile Ala Asp Gly Gly Val
            100                 105                 110

Leu Pro Asn Ile Asn Pro Met Leu Leu Pro Ser Lys Thr Lys Lys Ser
        115                 120                 125

Thr Glu Pro Glu His
        130

<210> SEQ ID NO 16
<211> LENGTH: 120
<212> TYPE: PRT
<213> ORGANISM: Tetrahymena thermophila

<400> SEQUENCE: 16

Met Ala Pro Lys Lys Ala Pro Ala Ala Ala Glu Lys Lys Val Lys
1               5                   10                  15

Lys Ala Pro Thr Thr Glu Lys Lys Asn Lys Lys Lys Arg Ser Glu Thr
                20                  25                  30

Phe Ala Ile Tyr Ile Phe Lys Val Leu Lys Gln Val His Pro Asp Val
            35                  40                  45

Gly Ile Ser Lys Lys Ala Met Asn Ile Met Asn Ser Phe Ile Asn Asp
        50                  55                  60

Ser Phe Glu Arg Ile Ala Leu Glu Ser Ser Lys Leu Val Arg Phe Asn
65                  70                  75                  80

Lys Arg Arg Thr Leu Ser Ser Arg Glu Val Gln Thr Ala Val Lys Leu
                85                  90                  95

Leu Leu Pro Gly Glu Leu Ala Arg His Ala Ile Ser Glu Gly Thr Lys
            100                 105                 110

Ala Val Thr Lys Phe Ser Ser Ser
        115                 120

<210> SEQ ID NO 17
<211> LENGTH: 136
<212> TYPE: PRT
<213> ORGANISM: Tetrahymena thermophila

<400> SEQUENCE: 17

Met Ala Arg Thr Lys Gln Thr Ala Arg Lys Ser Thr Gly Ala Lys Ala
1               5                   10                  15

Pro Arg Lys Gln Leu Ala Ser Lys Ala Ala Arg Lys Ser Ala Pro Ala
                20                  25                  30

Thr Gly Gly Ile Lys Lys Pro His Arg Phe Arg Pro Gly Thr Val Ala
            35                  40                  45

Leu Arg Glu Ile Arg Lys Tyr Gln Lys Ser Thr Asp Leu Leu Ile Arg
        50                  55                  60

Lys Leu Pro Phe Gln Arg Leu Val Arg Asp Ile Ala His Glu Phe Lys
65                  70                  75                  80

Ala Glu Leu Arg Phe Gln Ser Ser Ala Val Leu Ala Leu Gln Glu Ala
                85                  90                  95

Ala Glu Ala Tyr Leu Val Gly Leu Phe Glu Asp Thr Asn Leu Cys Ala
            100                 105                 110

Ile His Ala Arg Arg Val Thr Ile Met Thr Lys Asp Met Gln Leu Ala
        115                 120                 125

Arg Arg Ile Arg Gly Glu Arg Phe
            130                 135

<210> SEQ ID NO 18
<211> LENGTH: 103
<212> TYPE: PRT
<213> ORGANISM: Tetrahymena thermophila

<400> SEQUENCE: 18

Met Ala Gly Gly Lys Gly Gly Lys Gly Met Gly Lys Val Gly Ala Lys
1               5                   10                  15

Arg His Ser Arg Lys Ser Asn Lys Ala Ser Ile Glu Gly Ile Thr Lys
                20                  25                  30

Pro Ala Ile Arg Arg Leu Ala Arg Arg Gly Gly Val Lys Arg Ile Ser
            35                  40                  45

Ser Phe Ile Tyr Asp Asp Ser Arg Gln Val Leu Lys Ser Phe Leu Glu

```
                50                  55                  60
Asn Val Val Arg Asp Ala Val Thr Tyr Thr Glu His Ala Arg Arg Lys
 65                  70                  75                  80

Thr Val Thr Ala Met Asp Val Val Tyr Ala Leu Lys Arg Gln Gly Arg
                 85                  90                  95

Thr Leu Tyr Gly Phe Gly Gly
                100

<210> SEQ ID NO 19
<211> LENGTH: 256
<212> TYPE: PRT
<213> ORGANISM: Drosophila melanogaster

<400> SEQUENCE: 19

Met Ser Asp Ser Ala Val Ala Thr Ser Ala Ser Pro Val Ala Ala Pro
  1               5                  10                  15

Pro Ala Thr Val Glu Lys Lys Val Val Gln Lys Lys Ala Ser Gly Ser
                 20                  25                  30

Ala Gly Thr Lys Ala Lys Lys Ala Ser Ala Thr Pro Ser His Pro Pro
             35                  40                  45

Thr Gln Gln Met Val Asp Ala Ser Ile Lys Asn Leu Lys Glu Arg Gly
         50                  55                  60

Gly Ser Ser Leu Leu Ala Ile Lys Lys Tyr Ile Thr Ala Thr Tyr Lys
 65                  70                  75                  80

Cys Asp Ala Gln Lys Leu Ala Pro Phe Ile Lys Lys Tyr Leu Lys Ser
                 85                  90                  95

Ala Val Val Asn Gly Lys Leu Ile Gln Thr Lys Gly Lys Gly Ala Ser
                100                 105                 110

Gly Ser Phe Lys Leu Ser Ala Ser Ala Lys Lys Glu Lys Asp Pro Lys
            115                 120                 125

Ala Lys Ser Lys Val Leu Ser Ala Glu Lys Lys Val Gln Ser Lys Lys
        130                 135                 140

Val Ala Ser Lys Lys Ile Gly Val Ser Ser Lys Lys Thr Ala Val Gly
145                 150                 155                 160

Ala Ala Asp Lys Lys Pro Lys Ala Lys Lys Ala Val Ala Thr Lys Lys
                165                 170                 175

Thr Ala Glu Asn Lys Lys Thr Glu Lys Ala Lys Ala Lys Asp Ala Lys
                180                 185                 190

Lys Thr Gly Ile Ile Lys Ser Lys Pro Ala Thr Lys Ala Lys Val
            195                 200                 205

Thr Ala Ala Lys Pro Lys Ala Val Ala Lys Ala Ser Lys Ala Lys
        210                 215                 220

Pro Ala Val Ser Ala Lys Pro Lys Thr Val Lys Lys Ala Ser Val
225                 230                 235                 240

Ser Ala Thr Ala Lys Lys Pro Lys Ala Lys Thr Thr Ala Ala Lys Lys
                245                 250                 255

<210> SEQ ID NO 20
<211> LENGTH: 141
<212> TYPE: PRT
<213> ORGANISM: Drosophila melanogaster

<400> SEQUENCE: 20

Met Ala Gly Gly Lys Ala Gly Lys Asp Ser Gly Lys Ala Lys Ala Lys
  1               5                  10                  15

Ala Val Ser Arg Ser Ala Arg Ala Gly Leu Gln Phe Pro Val Gly Arg
```

```
                    20                  25                  30
Ile His Arg His Leu Lys Ser Arg Thr Thr Ser His Gly Arg Val Gly
            35                  40                  45
Ala Thr Ala Ala Val Tyr Ser Ala Ala Ile Leu Glu Tyr Leu Thr Ala
        50                  55                  60
Glu Val Leu Glu Leu Ala Gly Asn Ala Ser Lys Asp Leu Lys Val Lys
65                  70                  75                  80
Arg Ile Thr Pro Arg His Leu Gln Leu Ala Ile Arg Gly Asp Glu Glu
                85                  90                  95
Leu Asp Ser Leu Ile Lys Ala Thr Ile Ala Gly Gly Gly Val Ile Pro
            100                 105                 110
His Ile His Lys Ser Leu Ile Gly Lys Lys Glu Glu Thr Val Gln Asp
        115                 120                 125
Pro Gln Arg Lys Gly Asn Val Ile Leu Ser Gln Ala Tyr
    130                 135                 140

<210> SEQ ID NO 21
<211> LENGTH: 123
<212> TYPE: PRT
<213> ORGANISM: Drosophila melanogaster

<400> SEQUENCE: 21

Met Pro Pro Lys Thr Ser Gly Lys Ala Ala Lys Lys Ala Gly Lys Ala
1               5                   10                  15
Gln Lys Asn Ile Thr Lys Thr Asp Lys Lys Lys Arg Lys Arg Lys
            20                  25                  30
Glu Ser Tyr Ala Ile Tyr Ile Tyr Lys Val Leu Lys Gln Val His Pro
        35                  40                  45
Asp Thr Gly Ile Ser Ser Lys Ala Met Ser Ile Met Asn Ser Phe Val
    50                  55                  60
Asn Asp Ile Phe Glu Arg Ile Ala Ala Glu Ala Ser Arg Leu Ala His
65                  70                  75                  80
Tyr Asn Lys Arg Ser Thr Ile Thr Ser Arg Glu Ile Gln Thr Ala Val
                85                  90                  95
Arg Leu Leu Leu Pro Gly Glu Leu Ala Lys His Ala Val Ser Glu Gly
            100                 105                 110
Thr Lys Ala Val Thr Lys Tyr Thr Ser Ser Lys
        115                 120

<210> SEQ ID NO 22
<211> LENGTH: 136
<212> TYPE: PRT
<213> ORGANISM: Drosophila melanogaster

<400> SEQUENCE: 22

Met Ala Arg Thr Lys Gln Thr Ala Arg Lys Ser Thr Gly Gly Lys Ala
1               5                   10                  15
Pro Arg Lys Gln Leu Ala Thr Lys Ala Ala Arg Lys Ser Ala Pro Ala
            20                  25                  30
Thr Gly Gly Val Lys Lys Pro His Arg Tyr Arg Pro Gly Thr Val Ala
        35                  40                  45
Leu Arg Glu Ile Arg Arg Tyr Gln Lys Ser Thr Glu Leu Leu Ile Arg
    50                  55                  60
Lys Leu Pro Phe Gln Arg Leu Val Arg Glu Ile Ala Gln Asp Phe Lys
65                  70                  75                  80
Thr Asp Leu Arg Phe Gln Ser Ser Ala Val Met Ala Leu Gln Glu Ala
```

```
                    85                  90                  95

Ser Glu Ala Tyr Leu Val Gly Leu Phe Glu Asp Thr Asn Leu Cys Ala
                100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 23
<211> LENGTH: 103
<212> TYPE: PRT
<213> ORGANISM: Drosophila melanogaster

<400> SEQUENCE: 23

Met Thr Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
                100

<210> SEQ ID NO 24
<211> LENGTH: 208
<212> TYPE: PRT
<213> ORGANISM: Caenorhabditis elegans

<400> SEQUENCE: 24

Met Ser Asp Ser Ala Val Val Ala Ala Val Glu Pro Lys Val Pro
1               5                   10                  15

Lys Ala Lys Ala Ala Lys Ala Ala Lys Pro Thr Lys Val Ala Lys Ala
            20                  25                  30

Lys Ala Pro Val Ala His Pro Pro Tyr Ile Asn Met Ile Lys Glu Ala
        35                  40                  45

Ile Lys Gln Leu Lys Asp Arg Lys Gly Ala Ser Lys Gln Ala Ile Leu
    50                  55                  60

Lys Phe Ile Ser Gln Asn Tyr Lys Leu Gly Asp Asn Val Ile Gln Ile
65                  70                  75                  80

Asn Ala His Leu Arg Gln Ala Leu Lys Arg Gly Val Thr Ser Lys Ala
                85                  90                  95

Leu Val Gln Ala Ala Gly Ser Gly Ala Asn Gly Arg Phe Arg Val Pro
                100                 105                 110

Glu Lys Ala Ala Ala Lys Lys Pro Ala Ala Ala Lys Lys Pro Ala
            115                 120                 125

Ala Ala Lys Lys Pro Ala Ala Ala Lys Lys Ala Thr Gly Glu Lys Lys
        130                 135                 140

Ala Lys Lys Pro Ala Ala Ala Lys Pro Lys Lys Ala Thr Gly Asp
145                 150                 155                 160

Lys Lys Val Lys Lys Ala Lys Ser Pro Lys Lys Val Ala Lys Pro Ala
```

```
                    165                 170                 175
Ala Lys Lys Val Ala Lys Ser Pro Ala Lys Lys Ala Pro Lys Lys
                180                 185                 190
Ile Ala Lys Pro Ala Ala Lys Lys Ala Ala Lys Pro Ala Ala Lys Ala
            195                 200                 205

<210> SEQ ID NO 25
<211> LENGTH: 127
<212> TYPE: PRT
<213> ORGANISM: Caenorhabditis elegans

<400> SEQUENCE: 25

Met Ser Gly Arg Gly Lys Gly Gly Lys Ala Lys Thr Gly Gly Lys Ala
1               5                   10                  15

Lys Ser Arg Ser Ser Arg Ala Gly Leu Gln Phe Pro Val Gly Arg Leu
            20                  25                  30

His Arg Ile Leu Arg Lys Gly Asn Tyr Ala Gln Arg Val Gly Ala Gly
        35                  40                  45

Ala Pro Val Tyr Leu Ala Ala Val Leu Glu Tyr Leu Ala Ala Glu Val
    50                  55                  60

Leu Glu Leu Ala Gly Asn Ala Ala Arg Asp Asn Lys Lys Thr Arg Ile
65                  70                  75                  80

Ala Pro Arg His Leu Gln Leu Ala Val Arg Asn Asp Glu Glu Leu Asn
                85                  90                  95

Lys Leu Leu Ala Gly Val Thr Ile Ala Gln Gly Gly Val Leu Pro Asn
            100                 105                 110

Ile Gln Ala Val Leu Leu Pro Lys Lys Thr Gly Gly Asp Lys Glu
        115                 120                 125

<210> SEQ ID NO 26
<211> LENGTH: 122
<212> TYPE: PRT
<213> ORGANISM: Caenorhabditis elegans

<400> SEQUENCE: 26

Met Pro Pro Lys Pro Ser Ala Lys Gly Ala Lys Lys Ala Ala Lys Thr
1               5                   10                  15

Val Thr Lys Pro Lys Asp Gly Lys Lys Arg Arg His Ala Arg Lys Glu
            20                  25                  30

Ser Tyr Ser Val Tyr Ile Tyr Arg Val Leu Lys Gln Val His Pro Asp
        35                  40                  45

Thr Gly Val Ser Ser Lys Ala Met Ser Ile Met Asn Ser Phe Val Asn
    50                  55                  60

Asp Val Phe Glu Arg Ile Ala Ala Glu Ala Ser Arg Leu Ala His Tyr
65                  70                  75                  80

Asn Lys Arg Ser Thr Ile Ser Ser Arg Glu Ile Gln Thr Ala Val Arg
                85                  90                  95

Leu Ile Leu Pro Gly Glu Leu Ala Lys His Ala Val Ser Glu Gly Thr
            100                 105                 110

Lys Ala Val Thr Lys Tyr Thr Ser Ser Lys
        115                 120

<210> SEQ ID NO 27
<211> LENGTH: 136
<212> TYPE: PRT
<213> ORGANISM: Caenorhabditis elegans

<400> SEQUENCE: 27
```

```
Met Ala Arg Thr Lys Gln Thr Ala Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Ser Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Arg Ala Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 28
<211> LENGTH: 103
<212> TYPE: PRT
<213> ORGANISM: Caenorhabditis elegans

<400> SEQUENCE: 28

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Cys Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Lys Gln Leu Ala Thr Lys Ala Ala Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30
```

Lys Leu Ala Ala Thr Pro Lys
1               5

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Val Thr Lys Ala Gly Gly Ser Ala Ala Leu Ser Pro Ser Lys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Ala Gly Gly Ser Ala Ala Leu Ser Pro Ser Lys Lys
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Gly Ala Pro Ala Ala Ala Thr Ala Pro Ala Pro Thr Ala His Lys Ala
1               5                   10                  15

Lys

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Pro Ser Val Pro Lys Val Pro Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic

<400> SEQUENCE: 35

Leu Gly Leu Lys Ser Leu Val Ser Lys
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic

```
<400> SEQUENCE: 36

Ser Leu Val Ser Lys Gly Thr Leu Val Gln Thr Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Gly Thr Gly Ala Ser Gly Ser Phe Lys Leu Asn Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic

<400> SEQUENCE: 38

Lys Ala Ser Gly Pro Pro Val Ser Glu Leu Ile Thr Lys
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Synthetic

<400> SEQUENCE: 39

Ala Ser Gly Pro Pro Val Ser Glu Leu Ile Thr Lys Ala Val Ala Ala
1               5                   10                  15

Ser Lys

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Lys Ala Leu Ala Ala Ala Gly Tyr Asp Val Glu Lys
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Gly Thr Leu Val Gln Thr Lys Gly Thr Gly Ala Ser Gly Ser Phe Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic
```

<400> SEQUENCE: 42

Ala Leu Ala Ala Ala Gly Tyr Asp Val Glu Lys Asn Asn Ser Arg
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Synthetic

<400> SEQUENCE: 43

Lys Pro Ala Ala Ala Thr Val Thr Lys
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Ala Gly Gly Lys Ala Gly Lys Asp Ser Gly Lys
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Ala Gly Lys Asp Ser Gly Lys Ala Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Lys Thr Ser Ala Thr Val Gly Pro Lys
1               5

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Thr Ser Ala Thr Val Gly Pro Lys Ala Pro Ser Gly Gly Lys Lys
1               5                   10                  15

<210> SEQ ID NO 48
<211> LENGTH: 9
<212> TYPE: PRT
<213> ORGANISM: Artificial Sequence
<220> FEATURE:
<223> OTHER INFORMATION: Synthetic

```
<400> SEQUENCE: 48

Lys Ala Thr Gln Ala Ser Gln Glu Tyr
1               5

<210> SEQ ID NO 49
<211> LENGTH: 13
<212> TYPE: PRT
<213> ORGANISM: Artificial Sequence
<220> FEATURE:
<223> OTHER INFORMATION: Synthetic

<400> SEQUENCE: 49

Gly Lys Leu Glu Ala Ile Ile Thr Pro Pro Ala Lys
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Lys Gly Asn Tyr Ala Glu Arg
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic

<400> SEQUENCE: 51

Asn Asp Glu Glu Leu Asn Lys Leu Leu Gly Lys
1               5                   10

<210> SEQ ID NO 52
<211> LENGTH: 20
<212> TYPE: PRT
<213> ORGANISM: Artificial Sequence
<220> FEATURE:
<223> OTHER INFORMATION: Synthetic

<400> SEQUENCE: 52

Val Thr Ile Ala Gln Gly Gly Val Leu Pro Asn Ile Gln Ala Val Leu
1               5                   10                  15

Leu Pro Lys Lys
            20

<210> SEQ ID NO 53
<211> LENGTH: 11
<212> TYPE: PRT
<213> ORGANISM: Artificial Sequence
<220> FEATURE:
<223> OTHER INFORMATION: Synthetic

<400> SEQUENCE: 53

Pro Glu Pro Thr Lys Ser Ala Pro Ala Pro Lys
1               5                   10

<210> SEQ ID NO 54
<211> LENGTH: 10
<212> TYPE: PRT
<213> ORGANISM: Artificial Sequence
<220> FEATURE:
```

<223> OTHER INFORMATION: Synthetic

<400> SEQUENCE: 54

Ser Ala Pro Ala Pro Lys Lys Gly Ser Lys
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Gly Ser Lys Lys Ala Val Thr Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ala Val Thr Lys Ala Gln Lys
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Lys Glu Ser Tyr Ser Val Tyr Val Tyr Lys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic

<400> SEQUENCE: 58

His Ala Val Ser Glu Gly Thr Lys Ala Val Thr Lys
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

Ala Val Thr Lys Tyr Thr Ser Ser Lys
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Pro Glu Leu Ala Lys Ser Ala Pro Ala Pro Lys
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Lys Ala Val Thr Lys Val Gln Lys
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Ala Val Thr Lys Val Gln Lys Lys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Lys Ser Thr Gly Gly Lys Ala Pro Arg
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

Gln Leu Ala Thr Lys Ala Ala Arg
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Lys Ser Ala Pro Ala Thr Gly Gly Val Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic

```
<400> SEQUENCE: 66

Tyr Gln Lys Ser Thr Glu Leu Leu Ile Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Val Thr Ile Met Pro Lys Asp Ile Gln Leu Ala Arg
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Lys Ser Ala Pro Ser Thr Gly Gly Val Lys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Glu Ile Ala Gln Asp Phe Lys Thr Asp Leu Arg
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Gly Gly Lys Gly Leu Gly Lys
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Gly Leu Gly Lys Gly Gly Ala Lys Arg
1               5

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72
```

```
Asp Asn Ile Gln Gly Ile Thr Lys Pro Ala Ile Arg
1               5                   10
```

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

```
Asp Ala Val Thr Tyr Thr Glu His Ala Lys Arg
1               5                   10
```

<210> SEQ ID NO 74
<211> LENGTH: 13
<212> TYPE: PRT
<213> ORGANISM: Artificial Sequence
<220> FEATURE:
<223> OTHER INFORMATION: Synthetic

<400> SEQUENCE: 74

```
Thr Val Thr Ala Met Asp Val Val Tyr Ala Leu Lys Arg
1               5                   10
```

<210> SEQ ID NO 75
<211> LENGTH: 13
<212> TYPE: PRT
<213> ORGANISM: Artificial Sequence
<220> FEATURE:
<223> OTHER INFORMATION: Synthetic

<400> SEQUENCE: 75

```
Lys Thr Ser Gly Pro Pro Val Ser Glu Leu Ile Thr Lys
1               5                   10
```

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

```
Ala Val Ala Ala Ser Lys Glu Arg
1               5
```

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

```
Lys Ala Leu Ala Ala Gly Gly Tyr Asp Val Glu Lys
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

```
Leu Val Thr Thr Gly Val Leu Lys Gln Thr Lys
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Synthetic

<400> SEQUENCE: 79

Val Val Lys Val Lys Pro Val Lys
1               5

<210> SEQ ID NO 80
<211> LENGTH: 13
<212> TYPE: PRT
<213> ORGANISM: Artificial Sequence
<220> FEATURE:
<223> OTHER INFORMATION: Synthetic

<400> SEQUENCE: 80

Ala Gly Gly Lys Ala Gly Lys Asp Ser Gly Lys Ala Lys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic

<400> SEQUENCE: 81

Ala Gly Lys Asp Ser Gly Lys Ala Lys Thr Lys
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic

<400> SEQUENCE: 82

Asn Asp Glu Glu Leu Asn Lys Leu Leu Gly Arg
1               5                   10

<210> SEQ ID NO 83
<211> LENGTH: 19
<212> TYPE: PRT
<213> ORGANISM: Artificial Sequence
<220> FEATURE:
<223> OTHER INFORMATION: Synthetic

<400> SEQUENCE: 83

Ala Thr Ile Ala Gly Gly Gly Val Ile Pro His Ile His Lys Ser Leu
1               5                   10                  15

Ile Gly Lys

<210> SEQ ID NO 84
<211> LENGTH: 14
<212> TYPE: PRT
<213> ORGANISM: Artificial Sequence
<220> FEATURE:
<223> OTHER INFORMATION: Synthetic

<400> SEQUENCE: 84
```

```
Ser Ser Ala Thr Val Gly Pro Lys Ala Pro Ala Val Gly Lys
1               5                   10
```

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

```
Ala Pro Ala Val Gly Lys Lys
1               5
```

<210> SEQ ID NO 86
<211> LENGTH: 11
<212> TYPE: PRT
<213> ORGANISM: Artificial Sequence
<220> FEATURE:
<223> OTHER INFORMATION: Synthetic

<400> SEQUENCE: 86

```
Pro Asp Pro Ala Lys Ser Ala Pro Ala Pro Lys
1               5                   10
```

<210> SEQ ID NO 87
<211> LENGTH: 11
<212> TYPE: PRT
<213> ORGANISM: Artificial Sequence
<220> FEATURE:
<223> OTHER INFORMATION: Synthetic

<400> SEQUENCE: 87

```
Ser Ala Pro Ala Pro Lys Lys Gly Ser Lys Lys
1               5                   10
```

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

```
Ser Ala Pro Ala Pro Lys Lys Gly Ser Lys Lys Ala Ile Ser Lys
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

```
Pro Glu Pro Ala Lys Ser Ala Pro Ala Pro Lys Lys Gly Ser Lys
1               5                   10                  15
```

<210> SEQ ID NO 90
<211> LENGTH: 18
<212> TYPE: PRT
<213> ORGANISM: Artificial Sequence
<220> FEATURE:
<223> OTHER INFORMATION: Synthetic

<400> SEQUENCE: 90

```
Ser Ala Pro Ala Pro Lys Lys Gly Ser Lys Lys Ala Val Thr Lys Ala
1               5                   10                  15

Gln Lys
```

<210> SEQ ID NO 91
<211> LENGTH: 9
<212> TYPE: PRT
<213> ORGANISM: Artificial Sequence
<220> FEATURE:
<223> OTHER INFORMATION: Synthetic
<400> SEQUENCE: 91

```
Lys Gly Ser Lys Lys Ala Ile Ser Lys
1               5
```

<210> SEQ ID NO 92
<211> LENGTH: 12
<212> TYPE: PRT
<213> ORGANISM: Artificial Sequence
<220> FEATURE:
<223> OTHER INFORMATION: Synthetic
<400> SEQUENCE: 92

```
Lys Gly Ser Lys Lys Ala Val Thr Lys Ala Gln Lys
1               5                   10
```

<210> SEQ ID NO 93
<211> LENGTH: 9
<212> TYPE: PRT
<213> ORGANISM: Artificial Sequence
<220> FEATURE:
<223> OTHER INFORMATION: Synthetic
<400> SEQUENCE: 93

```
Lys Gly Ser Lys Lys Ala Val Thr Lys
1               5
```

<210> SEQ ID NO 94
<211> LENGTH: 12
<212> TYPE: PRT
<213> ORGANISM: Artificial Sequence
<220> FEATURE:
<223> OTHER INFORMATION: Synthetic
<400> SEQUENCE: 94

```
Lys Gly Ser Lys Lys Ala Leu Thr Lys Ala Gln Lys
1               5                   10
```

<210> SEQ ID NO 95
<211> LENGTH: 9
<212> TYPE: PRT
<213> ORGANISM: Artificial Sequence
<220> FEATURE:
<223> OTHER INFORMATION: Synthetic
<400> SEQUENCE: 95

```
Lys Ala Val Thr Lys Ala Gln Lys Lys
1               5
```

<210> SEQ ID NO 96
<211> LENGTH: 13
<212> TYPE: PRT
<213> ORGANISM: Artificial Sequence
<220> FEATURE:
<223> OTHER INFORMATION: Synthetic
<400> SEQUENCE: 96

```
Lys Gly Ser Lys Lys Ala Ile Ser Lys Ala Gln Lys Lys
1               5                   10

<210> SEQ ID NO 97
<211> LENGTH: 17
<212> TYPE: PRT
<213> ORGANISM: Artificial Sequence
<220> FEATURE:
<223> OTHER INFORMATION: Synthetic

<400> SEQUENCE: 97

Leu Leu Leu Pro Gly Glu Leu Ala Lys His Ala Val Ser Glu Gly Thr
1               5                   10                  15

Lys

<210> SEQ ID NO 98
<211> LENGTH: 6
<212> TYPE: PRT
<213> ORGANISM: Artificial Sequence
<220> FEATURE:
<223> OTHER INFORMATION: Synthetic

<400> SEQUENCE: 98

Lys Gln Leu Ala Thr Lys
1               5

<210> SEQ ID NO 99
<211> LENGTH: 18
<212> TYPE: PRT
<213> ORGANISM: Artificial Sequence
<220> FEATURE:
<223> OTHER INFORMATION: Synthetic

<400> SEQUENCE: 99

Thr Ser Gly Pro Pro Val Ser Glu Leu Ile Thr Lys Ala Val Ala Ala
1               5                   10                  15

Ser Lys

<210> SEQ ID NO 100
<211> LENGTH: 14
<212> TYPE: PRT
<213> ORGANISM: Artificial Sequence
<220> FEATURE:
<223> OTHER INFORMATION: Synthetic

<400> SEQUENCE: 100

Gly Lys Gly Gly Lys Gly Leu Gly Lys Gly Gly Ala Lys Arg
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

Gly Leu Gly Lys Gly Gly Ala Lys
1               5

<210> SEQ ID NO 102
<211> LENGTH: 10
<212> TYPE: PRT
<213> ORGANISM: Artificial Sequence
<220> FEATURE:
```

<223> OTHER INFORMATION: Synthetic

<400> SEQUENCE: 102

Tyr Gln Lys Ser Thr Glu Leu Leu Val Arg
1               5                   10

<210> SEQ ID NO 103
<211> LENGTH: 220
<212> TYPE: PRT
<213> ORGANISM: Mus musculus

<400> SEQUENCE: 103

Ser Glu Thr Ala Pro Ala Ala Pro Ala Ala Pro Ala Pro Val Glu Lys
1               5                   10                  15

Thr Pro Val Lys Lys Lys Ala Lys Lys Thr Gly Ala Ala Ala Gly Lys
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Thr Ala Lys Lys Thr Pro Lys Lys Ala Lys Lys
145                 150                 155                 160

Pro Ala Ala Ala Gly Ala Lys Lys Val Ser Lys Ser Pro Lys Lys
                165                 170                 175

Val Lys Ala Ala Lys Pro Lys Ala Ala Lys Ser Pro Ala Lys Ala
            180                 185                 190

Lys Ala Pro Lys Ala Lys Ala Ser Lys Pro Lys Ala Ser Lys Pro Lys
        195                 200                 205

Ala Thr Lys Ala Lys Lys Ala Ala Pro Arg Lys Lys
    210                 215                 220

<210> SEQ ID NO 104
<211> LENGTH: 142
<212> TYPE: PRT
<213> ORGANISM: Mus musculus

<400> SEQUENCE: 104

Ser Gly Arg Gly Lys Thr Gly Gly Lys Ala Arg Ala Lys Ala Lys Ser
1               5                   10                  15

Arg Ser Ser Arg Ala Gly Leu Gln Phe Pro Val Gly Arg Val His Arg
            20                  25                  30

Leu Leu Arg Lys Gly His Tyr Ala Glu Arg Val Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ala Arg Asp Asn Lys Lys Thr Arg Ile Ile Pro
65                  70                  75                  80

```
Arg His Leu Gln Leu Ala Ile Arg Asn Asp Glu Glu Leu Asn Lys Leu
                85                  90                  95

Leu Gly Gly Val Thr Ile Ala Gln Gly Val Leu Pro Asn Ile Gln
            100                 105                 110

Ala Val Leu Leu Pro Lys Lys Ser Ser Ala Thr Val Gly Pro Lys Ala
        115                 120                 125

Pro Ala Val Gly Lys Lys Ala Ser Gln Ala Ser Gln Glu Tyr
    130                 135                 140

<210> SEQ ID NO 105
<211> LENGTH: 125
<212> TYPE: PRT
<213> ORGANISM: Mus musculus

<400> SEQUENCE: 105

Pro Glu Pro Ala Lys Ser Ala Pro Ala Pro Lys Lys Gly Ser Lys Lys
1               5                   10                  15

Ala Val Thr Lys Ala Gln Lys Lys Asp Gly Lys Lys Arg Lys Arg Ser
            20                  25                  30

Arg Lys Glu Ser Tyr Ser Val Tyr Val Tyr Lys Val Leu Lys Gln Val
        35                  40                  45

His Pro Asp Thr Gly Ile Ser Ser Lys Ala Met Gly Ile Met Asn Ser
    50                  55                  60

Phe Val Asn Asp Ile Phe Glu Arg Ile Ala Ser Glu Ala Ser Arg Leu
65                  70                  75                  80

Ala His Tyr Asn Lys Arg Ser Thr Ile Thr Ser Arg Glu Ile Gln Thr
                85                  90                  95

Ala Val Arg Leu Leu Leu Pro Gly Glu Leu Ala Lys His Ala Val Ser
            100                 105                 110

Glu Gly Thr Lys Ala Val Thr Lys Tyr Thr Ser Ser Lys
        115                 120                 125

<210> SEQ ID NO 106
<211> LENGTH: 135
<212> TYPE: PRT
<213> ORGANISM: Mus musculus

<400> SEQUENCE: 106

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135
```

<210> SEQ ID NO 107
<211> LENGTH: 102
<212> TYPE: PRT
<213> ORGANISM: Mus musculus

<400> SEQUENCE: 107

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
50                  55                  60

Val Ile Arg Asp Ala Val Thr Tyr Thr Glu His Ala Lys Arg Lys Thr
65                  70                  75                  80

Val Thr Ala Met Asp Val Val Tyr Ala Leu Lys Arg Gln Gly Arg Thr
                85                  90                  95

Leu Tyr Gly Phe Gly Gly
            100

<210> SEQ ID NO 108
<211> LENGTH: 211
<212> TYPE: PRT
<213> ORGANISM: Mus musculus

<400> SEQUENCE: 108

Ser Glu Ala Ala Pro Ala Ala Pro Ala Ala Pro Pro Ala Glu Lys
1               5                   10                  15

Ala Pro Ala Lys Lys Ala Ala Lys Lys Pro Ala Gly Val Arg Arg
            20                  25                  30

Lys Ala Ser Gly Pro Pro Val Ser Glu Leu Ile Thr Lys Ala Val Ala
            35                  40                  45

Ala Ser Lys Glu Arg Ser Gly Val Ser Leu Ala Ala Leu Lys Lys Ala
50                  55                  60

Leu Ala Ala Ala Gly Tyr Asp Val Glu Lys Asn Asn Ser Arg Ile Lys
65                  70                  75                  80

Leu Gly Leu Lys Ser Leu Val Ser Lys Gly Ile Leu Val Gln Thr Lys
                85                  90                  95

Gly Thr Gly Ala Ser Gly Ser Phe Lys Leu Asn Lys Lys Ala Ala Ser
            100                 105                 110

Gly Glu Ala Lys Pro Gln Ala Lys Lys Ala Gly Ala Ala Lys Ala Lys
        115                 120                 125

Lys Pro Ala Gly Ala Ala Lys Lys Pro Lys Lys Ala Thr Gly Ala Ala
    130                 135                 140

Thr Pro Lys Lys Ala Ala Lys Lys Thr Pro Lys Lys Ala Lys Lys Pro
145                 150                 155                 160

Ala Ala Ala Ala Val Thr Lys Val Ala Lys Ser Pro Lys Ala
                165                 170                 175

Lys Val Thr Lys Pro Lys Lys Val Lys Ser Ala Ser Lys Ala Val Lys
            180                 185                 190

Pro Lys Ala Ala Lys Pro Lys Val Ala Lys Lys Val Ala Ala
        195                 200                 205

Lys Lys Lys
    210

<210> SEQ ID NO 109
<211> LENGTH: 129
<212> TYPE: PRT
<213> ORGANISM: Mus musculus

<400> SEQUENCE: 109

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr Ser Glu Arg Val Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ala Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Arg Val Thr Ile Ala Gln Gly Gly Val Leu Pro Asn Ile Gln
            100                 105                 110

Ala Val Leu Leu Pro Lys Lys Thr Glu Ser His His Lys Ala Lys Gly
        115                 120                 125

Lys

<210> SEQ ID NO 110
<211> LENGTH: 125
<212> TYPE: PRT
<213> ORGANISM: Mus musculus

<400> SEQUENCE: 110

Pro Glu Pro Ala Lys Ser Ala Pro Ala Pro Lys Lys Gly Ser Lys Lys
1               5                   10                  15

Ala Val Thr Lys Ala Gln Lys Lys Asp Gly Lys Lys Arg Lys Arg Ser
            20                  25                  30

Arg Lys Glu Ser Tyr Ser Val Tyr Val Tyr Lys Val Leu Lys Gln Val
        35                  40                  45

His Pro Asp Thr Gly Ile Ser Ser Lys Ala Met Gly Ile Met Asn Ser
    50                  55                  60

Phe Val Asn Asp Ile Phe Glu Arg Ile Ala Gly Glu Ala Ser Arg Leu
65                  70                  75                  80

Ala His Tyr Asn Lys Arg Ser Thr Ile Thr Ser Arg Glu Ile Gln Thr
                85                  90                  95

Ala Val Arg Leu Leu Leu Pro Gly Glu Leu Ala Lys His Ala Val Ser
            100                 105                 110

Glu Gly Thr Lys Ala Val Thr Lys Tyr Thr Ser Ser Lys
        115                 120                 125

<210> SEQ ID NO 111
<211> LENGTH: 135
<212> TYPE: PRT
<213> ORGANISM: Mus musculus

<400> SEQUENCE: 111

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr

```
                    20                  25                  30
Gly Gly Val Lys Lys Pro His Arg Tyr Arg Pro Gly Thr Val Ala Leu
            35                  40                  45
Arg Glu Ile Arg Arg Tyr Gln Lys Ser Thr Glu Leu Leu Ile Arg Lys
    50                  55                  60
Leu Pro Phe Gln Arg Leu Val Arg Glu Ile Ala Gln Asp Phe Lys Thr
65                  70                  75                  80
Asp Leu Arg Phe Gln Ser Ser Ala Val Met Ala Leu Gln Glu Ala Cys
                85                  90                  95
Glu Ala Tyr Leu Val Gly Leu Phe Glu Asp Thr Asn Leu Cys Ala Ile
            100                 105                 110
His Ala Lys Arg Val Thr Ile Met Pro Lys Asp Ile Gln Leu Ala Arg
        115                 120                 125
Arg Ile Arg Gly Glu Arg Ala
    130                 135

<210> SEQ ID NO 112
<211> LENGTH: 102
<212> TYPE: PRT
<213> ORGANISM: Mus musculus

<400> SEQUENCE: 112

Ser Gly Arg Gly Lys Gly Gly Lys Gly Leu Gly Lys Gly Gly Ala Lys
1               5                   10                  15
Arg His Arg Lys Val Leu Arg Asp Asn Ile Gln Gly Ile Thr Lys Pro
            20                  25                  30
Ala Ile Arg Arg Leu Ala Arg Arg Gly Gly Val Lys Arg Ile Ser Gly
        35                  40                  45
Leu Ile Tyr Glu Glu Thr Arg Gly Val Leu Lys Val Phe Leu Glu Asn
    50                  55                  60
Val Ile Arg Asp Ala Val Thr Tyr Thr Glu His Ala Lys Arg Lys Thr
65                  70                  75                  80
Val Thr Ala Met Asp Val Val Tyr Ala Leu Lys Arg Gln Gly Arg Thr
                85                  90                  95
Leu Tyr Gly Phe Gly Gly
            100

<210> SEQ ID NO 113
<211> LENGTH: 11
<212> TYPE: PRT
<213> ORGANISM: Artificial Sequence
<220> FEATURE:
<223> OTHER INFORMATION: Synthetic

<400> SEQUENCE: 113

Pro Glu Pro Ala Lys Ser Ala Pro Ala Pro Lys
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

Ser Ser Ser Ser Ser Ser Lys Leu Ser Lys Ser Ser Lys
1               5                   10
```

```
<210> SEQ ID NO 115
<211> LENGTH: 13
<212> TYPE: PRT
<213> ORGANISM: Artificial Sequence
<220> FEATURE:
<223> OTHER INFORMATION: Synthetic

<400> SEQUENCE: 115

Lys Lys Ala Pro Pro Ser Lys Thr Gly Ser Lys Arg Arg
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic

<400> SEQUENCE: 116

Gly Pro Gly Lys Leu Ser Lys Ala Ala Ala Leu Ala Ser
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic

<400> SEQUENCE: 117

Ala Thr Pro Ala Ala Ser Lys Ser Glu Pro Val Gln Ala
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic

<400> SEQUENCE: 118

Leu Lys Ser Leu Val Ser Lys Gly Thr Leu Val Gln Thr
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Synthetic

<400> SEQUENCE: 119

Lys Ala Val Ala Ala Ser Lys Glu Arg Ser Gly Val Ser
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Pro Lys Lys Gly Ser Lys Lys Ala Ile Thr Lys Ala
1               5                   10

<210> SEQ ID NO 121
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 121

Ala Pro Lys Lys Gly Ser Lys Lys Ala Val Thr Lys Ala
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic

<400> SEQUENCE: 122

Lys Ala Val Ala Ala Ser Lys Glu Arg Asn Gly Leu Ser
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic

<400> SEQUENCE: 123

Ile Lys Ser Leu Val Ser Lys Gly Thr Leu Val Gln Thr
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic

<400> SEQUENCE: 124

Lys Ser Lys Pro Lys Arg Lys Ser Thr Pro Lys Ser Ala
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Synthetic

<400> SEQUENCE: 125

Ala Pro Ser Lys Pro Gly Lys Ala Ser Pro Ser Ala Arg
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Synthetic

<400> SEQUENCE: 126

Pro Thr Pro Ala Leu Pro Lys Leu Gly Pro Val Pro Pro
1               5                   10

<210> SEQ ID NO 127
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 127

Ser Leu Thr Arg Ser Lys Lys Gln Gln Pro Ala Thr Val
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Synthetic

<400> SEQUENCE: 128

Gly Arg Arg Thr Val Lys Lys Thr Leu Pro Pro Lys Glu
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthetic

<400> SEQUENCE: 129

Leu Ala Ala Val Ala Gln Lys Lys Arg Pro Leu Val Ser
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic

<400> SEQUENCE: 130

Leu Val Glu Ser Thr Ala Lys Gly Leu Pro Arg Arg Lys
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic

<400> SEQUENCE: 131

Ala Thr Lys Ala Ala Arg Lys Ser Ala Pro Ser Thr Gly
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Synthetic

<400> SEQUENCE: 132

Gln Lys Gly Glu Arg Leu Lys Asn Tyr Pro Gly Arg Leu
1               5                   10

<210> SEQ ID NO 133
<211> LENGTH: 13
<212> TYPE: PRT
```

<213> ORGANISM: Artificial Sequence
<220> FEATURE:
<223> OTHER INFORMATION: Synthetic

<400> SEQUENCE: 133

Val Glu Leu Gly Asn Leu Lys Asn Arg Pro Gly Glu Leu
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic

<400> SEQUENCE: 134

Lys Ser Lys Pro Ala Lys Lys Ala Ala Ala Ala Lys Ala
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Synthetic

<400> SEQUENCE: 135

Ala Ala Gly Ser Leu Ala Lys Leu Ala Ser Ser Arg Ser
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Synthetic

<400> SEQUENCE: 136

Ser Gly Leu Ala Gln Pro Lys Gly Ala Pro Lys Thr Lys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Synthetic

<400> SEQUENCE: 137

Glu Lys Thr Lys Thr Thr Lys Ser Ala Val Leu Ala Arg
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic

<400> SEQUENCE: 138

Val Pro Ser Arg Lys Leu Lys Thr Ala Glu Arg Glu Pro
1               5                   10

<210> SEQ ID NO 139
<211> LENGTH: 13
<212> TYPE: PRT
<213> ORGANISM: Artificial Sequence

```
<220> FEATURE:
<223> OTHER INFORMATION: Synthetic

<400> SEQUENCE: 139

Arg Val Ala Thr Gln Gly Lys Lys Ala Lys Val Gln Gln
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Synthetic

<400> SEQUENCE: 140

Gly Gln Pro Gln Thr Arg Lys Gln Ala Thr Pro Val Leu
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Synthetic

<400> SEQUENCE: 141

Leu Pro Gly Glu Leu Ala Lys His Ala Val Ser Glu Gly
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Synthetic

<400> SEQUENCE: 142

Thr Pro Lys Lys Ala Lys Lys Pro Ala Ala Ala Thr Val
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Synthetic

<400> SEQUENCE: 143

Asn Ile Gln Gly Ile Thr Lys Pro Ala Ile Arg Arg Leu
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic

<400> SEQUENCE: 144

Gly Lys Ser Lys Gly Gly Lys Phe Gly Lys Lys Lys Lys
1               5                   10

<210> SEQ ID NO 145
<211> LENGTH: 13
<212> TYPE: PRT
<213> ORGANISM: Artificial Sequence
<220> FEATURE:
```

<223> OTHER INFORMATION: Synthetic

<400> SEQUENCE: 145

Ser Ser Gly Ser Lys Gln Lys Gly Gly Phe Ser Gly Gly
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic

<400> SEQUENCE: 146

Ala Gly Lys Leu Leu Lys Ala Gly Ala Gly Thr Ser
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic

<400> SEQUENCE: 147

Arg Thr Arg Gly Val Thr Lys Thr Gly Arg Thr Val Thr
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic

<400> SEQUENCE: 148

Glu Arg Leu Glu Ala Lys Lys Leu Gly Val Pro Ser Glu
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 149

Thr Xaa Thr Thr Thr Arg Lys Val Gly Gln Arg Ala Leu
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Synthetic

<400> SEQUENCE: 150

Leu Pro Gly Glu Leu Ala Lys Asp Gly Val Ser Glu Gly
1               5                   10

<210> SEQ ID NO 151
<211> LENGTH: 13

```
<212> TYPE: PRT
<213> ORGANISM: Artificial Sequence
<220> FEATURE:
<223> OTHER INFORMATION: Synthetic

<400> SEQUENCE: 151

Lys Ser Ala Pro Ala Pro Lys Lys Gly Ser Lys Lys Ala
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic

<400> SEQUENCE: 152

Met Ala Lys Lys Val Thr Lys Ala Gly Gly Ser Ala Ala
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic

<400> SEQUENCE: 153

Ala Gly Lys Gly Leu Gly Lys Gly Gly Ala Lys Cys His
1               5                   10
```